(12) United States Patent
Smith et al.

(10) Patent No.: US 8,685,936 B2
(45) Date of Patent: Apr. 1, 2014

(54) SPHINGOSINE KINASE INHIBITOR PRODRUGS

(75) Inventors: Charles D. Smith, Mount Pleasant, SC (US); Yan Zhuang, Hershey, PA (US); Lynn W. Maines, Hummelstown, PA (US)

(73) Assignee: Apogee Biotechnology Corporation, Hershey, PA (US)

( * ) Notice: Subject to any disclaimer, the term of this patent is extended or adjusted under 35 U.S.C. 154(b) by 138 days.

(21) Appl. No.: 13/255,813

(22) PCT Filed: Mar. 12, 2010

(86) PCT No.: PCT/US2010/027177
§ 371 (c)(1),
(2), (4) Date: Nov. 18, 2011

(87) PCT Pub. No.: WO2010/105183
PCT Pub. Date: Sep. 16, 2010

(65) Prior Publication Data
US 2012/0058966 A1    Mar. 8, 2012

Related U.S. Application Data

(60) Provisional application No. 61/159,723, filed on Mar. 12, 2009.

(51) Int. Cl.
| | | |
|---|---|---|
| A61K 31/70 | (2006.01) | |
| A61K 31/66 | (2006.01) | |
| A61K 31/27 | (2006.01) | |
| C07H 17/00 | (2006.01) | |
| C07C 269/00 | (2006.01) | |
| C07F 9/02 | (2006.01) | |

(52) U.S. Cl.
USPC ............ 514/35; 514/107; 514/480; 514/617; 536/17.9; 560/158; 564/15; 564/180

(58) Field of Classification Search
None
See application file for complete search history.

(56) References Cited

U.S. PATENT DOCUMENTS

| | | |
|---|---|---|
| 7,338,961 B2 | 3/2008 | Smith et al. |
| 2008/0167352 A1* | 7/2008 | Smith et al. ................. 514/357 |
| 2009/0163545 A1 | 6/2009 | Goldfarb |
| 2012/0122870 A1 | 5/2012 | Smith |

* cited by examiner

*Primary Examiner* — Traviss C McIntosh, III
(74) *Attorney, Agent, or Firm* — McDonnell Boehnen Hulbert & Berghoff LLP

(57) ABSTRACT

The invention relates to prodrugs of hydroxyl-substituted adamantane compounds, pharmaceutical compositions thereof, and methods for inhibiting sphingosine kinase and for treating or preventing hyperproliferative disease, inflammatory disease, or angiogenic disease.

28 Claims, 7 Drawing Sheets

**p<0.01 vs. veh
* p<0.05 vs. veh

SPHINGOSINE KINASE INHIBITOR PRODRUGS

CROSS-REFERENCE TO RELATED APPLICATIONS

This application is a U.S. national phase application of International Patent Application No. PCT/US2010/027177, filed on Mar. 12, 2010, which claims the priority of U.S. Provisional Patent Application Ser. No. 61/159,723, filed Mar. 12, 2009, each of which is hereby incorporated herein by reference in its entirety.

GOVERNMENT SPONSORSHIP

This invention was made with government support through Grant R44 DK071395 awarded by the United States Public Health Service. Accordingly, the US government may have certain rights in this invention.

FIELD OF THE INVENTION

The invention relates to prodrug compounds whose metabolites are capable of inhibiting sphingosine kinase, and to pharmaceutical compositions comprising these compounds. The invention also relates to methods for the use of these compounds and pharmaceutical compositions for treating or preventing hyperproliferative disease, inflammatory disease, or angiogenic disease.

BACKGROUND OF THE INVENTION

The mechanisms and effects of the interconversion of sphingolipids have been the subjects of a growing body of scientific investigation. Sphingomyelin is a building block for cellular membranes and serves as the precursor for potent lipid messengers that have profound cellular effects. As described below, metabolism of these lipids is critically involved in the biology of hyperproliferative, inflammatory and angiogenic diseases. Consequently, manipulation of these metabolic pathways is a method for the therapy of a variety of diseases.

Ceramide is produced by the hydrolysis of sphingomyelin in response to several stimuli, including growth factors and inflammatory cytokines Ceramide can be hydrolyzed by the action of ceramidase to produce sphingosine. Sphingosine is then phosphorylated by sphingosine kinase (SK) to produce sphingosine-1-phosphate (S1P). Evidence demonstrates that S1P is a critical second messenger that exerts proliferative and anti-apoptotic actions. Additionally, ceramide enhances apoptosis in response to anticancer drugs including Taxol and etoposide. Furthermore, ceramide appears to induce apoptosis in tumor cells without killing quiescent normal cells. Studies in various cell lines consistently indicate that S1P is able to induce proliferation and protect cells from apoptosis. Together, the data demonstrate that the balance between cellular levels of ceramide and S1P determines if a cell proliferates. Therefore, altering this balance by reducing the production of S1P within hyperproliferating cells is an effective method to treat disorders arising from abnormal cell proliferation.

Sphingosine kinase is responsible for S1P production in cells. RNA encoding SK is expressed in most tissues, with higher levels often occurring in tumor tissue than in corresponding normal tissue. A variety of proliferative factors, including Protein Kinase C (PKC) activators, fetal calf serum, Platelet-Derived Growth Factor, Epidermal Growth Factor, and Tumor Necrosis Factor-alpha (TNFα) rapidly elevate cellular SK activity. This promotes proliferation and inhibits apoptosis of the target cells. Additionally, an oncogenic role of SK has been demonstrated. Conversely, inhibition of SK by transfection with a dominant-negative SK mutant or by treatment of cells with the nonspecific SK inhibitor D-erythro-N,N-dimethylsphingosine (DMS) blocks transformation mediated by oncogenic H-Ras. Since abnormal activation of Ras, as well as overexpression and mutation of ras family genes, frequently occurs in different cancers, these findings indicate a significant role of SK in these diseases.

In addition, S1P has been shown to have several important effects on cells that mediate immune functions. Platelets, monocytes and mast cells secrete S1P upon activation, promoting inflammatory cascades at the site of tissue damage. Activation of SK is required for the signaling responses since the ability of TNFα to induce adhesion molecule expression via activation of Nuclear Factor Kappa B (NFκB) is mimicked by S1P and is blocked by DMS. Similarly, S1P mimics the ability of TNFα to induce the expression of Cyclooxygenase-2 (COX-2) and the synthesis of prostaglandin $E_2$ ($PGE_2$), and knock-down of SK by RNA interference blocks these responses to TNFα. S1P is also a mediator of calcium influx during neutrophil activation by TNFα and other stimuli, leading to the production of superoxide and other toxic radicals. Therefore, reducing the production of S1P within immune cells and their target tissues may be an effective method to treat disorders arising from abnormal inflammation. Examples of such disorders include inflammatory bowel disease, arthritis, atherosclerosis, asthma, allergy, inflammatory kidney disease, circulatory shock, ischemia-reperfusion injury, post-surgical organ failure, organ transplantation, multiple sclerosis, chronic obstructive pulmonary disease, skin inflammation, periodontal disease, psoriasis and T cell-mediated diseases of immunity.

Angiogenesis refers to the state in the body in which various growth factors or other stimuli promote the formation of new blood vessels, and this process is critical to the pathology of a variety of diseases. In each case, excessive angiogenesis allows the progression of the disease and/or produces undesired effects in the patient. Since conserved biochemical mechanisms regulate the proliferation of vascular endothelial cells that form these new blood vessels, identification of methods to inhibit these mechanisms are expected to have utility for the treatment and prevention of a variety of diseases. More specifically, certain growth factors have been identified that lead to pathogenic angiogenesis. For example, Vascular Endothelial Growth Factor (VEGF) has angiogenic and mitogenic capabilities. Specifically, VEGF induces vascular endothelial cell proliferation, favoring the formation of new blood vessels. Sphingosine kinase is an important mediator of the actions of VEGF. For example, SK has been shown to mediate VEGF-induced activation of protein kinases. Production of S1P by SK stimulates NFκB activity leading to the production of COX-2, adhesion molecules and additional VEGF and other cytokines, all of which promote angiogenesis. Furthermore, the expression of endothelial isoforms of nitric oxide synthase (eNOS) is regulated by SK, and eNOS too subsequently modulates angiogenesis. Therefore, reducing the production of S1P within endothelial cells is likely to be an effective method to treat disorders arising from abnormal angiogenesis. Examples of such disorders include arthritis, cancer, psoriasis, Kaposi's sarcoma, hemangiomas, myocardial angiogenesis, atherosclerosis, and ocular angiogenic diseases.

Accordingly, there remains a need for improved inhibitors of SK are required for use as antiproliferative, anti-inflammatory and anti-angiogenic agents.

SUMMARY OF THE INVENTION

The invention relates generally to the compounds of formula (I), shown below, pharmaceutical compositions containing such compounds, and methods employing such compounds or compositions in the treatment or prevention of hyperproliferative disease, inflammatory disease, or angiogenic disease. More specifically, the invention relates to compounds that are prodrugs that are metabolized to compounds that are capable of inhibiting SK. These prodrugs can be, for example, alkyl esters, succinates, amino acid esters, carbamates, phosphates and glucosides.

In one aspect, the invention provides compounds of formula (I):

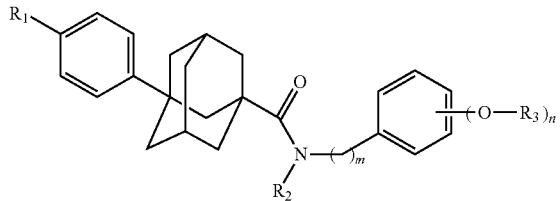

(I)

and pharmaceutically acceptable salts thereof, wherein
  $R_1$ is H, Cl or F;
  $R_2$ is H or alkyl;
  m is 0, 1 or 2;
  n is 1, 2, 3, 4 or 5;
  each $R_3$ is independently H, —C(O)alkyl, —C(O)CH$_2$CH$_2$C(O)OH, $R_4$, —C(O)NR$_5$R$_6$, —P(O)(OR$_7$)$_2$ or glucosyl, provided that at least one $R_3$ is not H,
  wherein
    $R_4$ is a natural or unnatural amino acid linked through the carboxyl moiety as an ester,
    $R_5$ is H or alkyl,
    $R_6$ is H or alkyl, and
    each $R_7$ is independently H or alkyl.

General terms for these compounds include alkyl esters, succinates, amino acid esters, carbamates, phosphates and glucosides.

The invention also provides pharmaceutical compositions comprising a compound or salt of formula (I) and at least one pharmaceutically acceptable carrier, solvent, adjuvant or diluent.

The invention also provides methods for the treatment or prevention of hyperproliferative disease, inflammatory disease, or angiogenic disease.

or 2% DSS in the drinking water and oral administration of 50 mg/kg Compound 1 or Compound 2 twice daily in Vehicle. After 6 days, the animals were sacrificed and the length of the colon was measured. Values represent the mean±std. dev. for 6-7 mice per group. In this model, colon length decreases as the disease progresses. The data demonstrate that both Compounds 1 and 2 reduce colitis-induced colon contraction, with Compound 2 being more efficacious than Compound 1.

Figure 9:
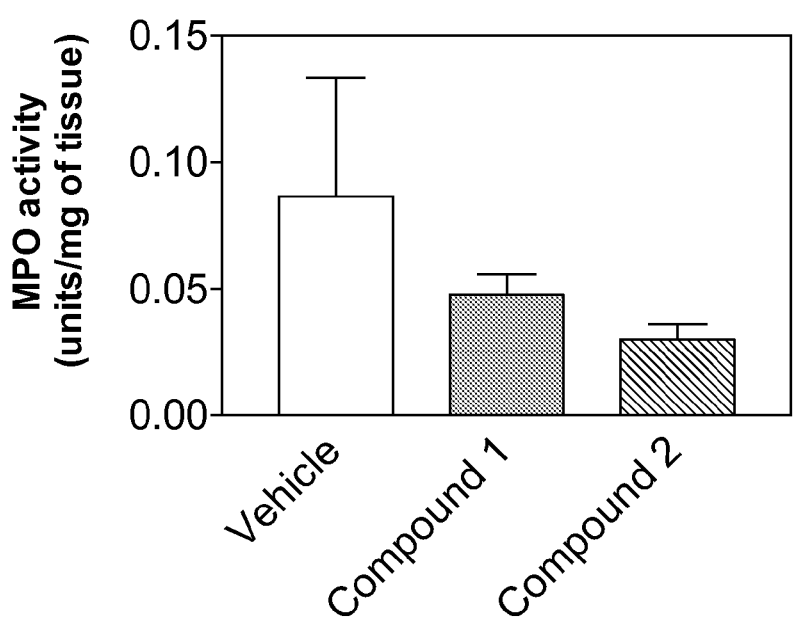

FIG. 9. Effects of Compound 1 and Compound 2 on neutrophil infiltration into the colon in the acute DSS-colitis model. C57BL/6 mice were treated for 6 days as follows: 2% DSS in the drinking water and daily oral administration of Vehicle (described in FIG. 7); or 2% DSS in the drinking water and oral administration of 50 mg/kg Compound 1 or Compound 2 in Vehicle. After 6 days, the animals were sacrificed and the colons were harvested. Myeloperoxidase activity (MPO) was measured and normalized by the protein concentration of the samples. Values represent the mean±std. dev. for 6-7 mice per group. In this model, MPO activity in the colon increases as a result of neutrophil infiltration into the colon as the disease progresses. The data demonstrate that both Compounds 1 and 2 reduce colitis-induced neutrophil infiltration into the colon, with Compound 2 being more efficacious than Compound 1.

Figure 10:
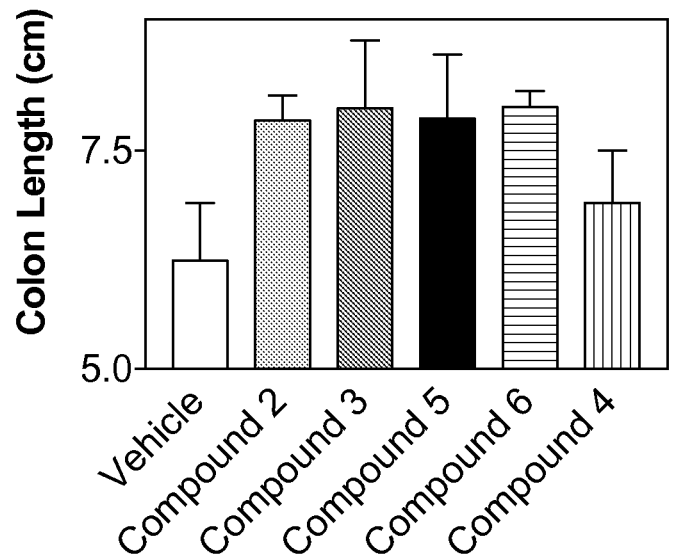

FIG. 10. Effects of ester prodrugs on colon length in the acute DSS-colitis model. C57BL/6 mice were treated for 6 days as follows: 2% DSS in the drinking water and daily oral administration of Vehicle (described in FIG. 7); or 2% DSS in the drinking water and oral administration of 50 mg/kg the indicated ester prodrugs in Vehicle. After 6 days, the animals were sacrificed and the length of the colon was measured. Values represent the mean±std. dev. for 4-5 mice per group. In this model, colon length decreases as the disease progresses. The data demonstrate that each of the ester prodrugs protects against colitis-induced colon contraction.

Figure 11:
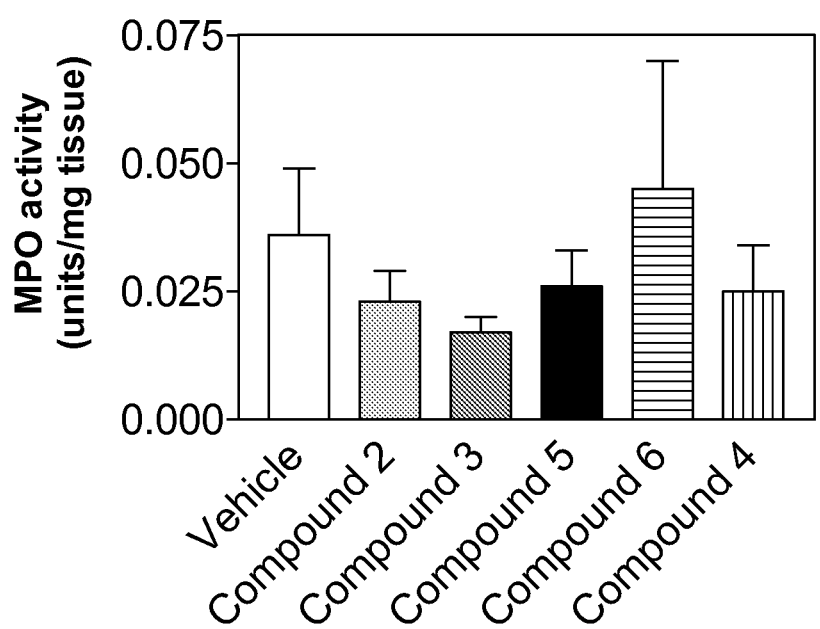

FIG. 11. Effects of ester prodrugs on neutrophil infiltration into the colon in the acute DSS-colitis model. C57BL/6 mice were treated for 6 days as follows: 2% DSS in the drinking water and daily oral administration of Vehicle (described in FIG. 7); or 2% DSS in the drinking water and oral administration of 50 mg/kg the indicated ester prodrugs in Vehicle. After 6 days, the animals were sacrificed and the length of the colon was measured. Values represent the mean±std. dev. for 4-5 mice per group. In this model, MPO activity increases as a result of neutrophil infiltration into the colon as the disease progresses. The data demonstrate that, with the exception of Compound 6, each of the ester prodrugs reduces neutrophil infiltration into the colon.

Figure 12:
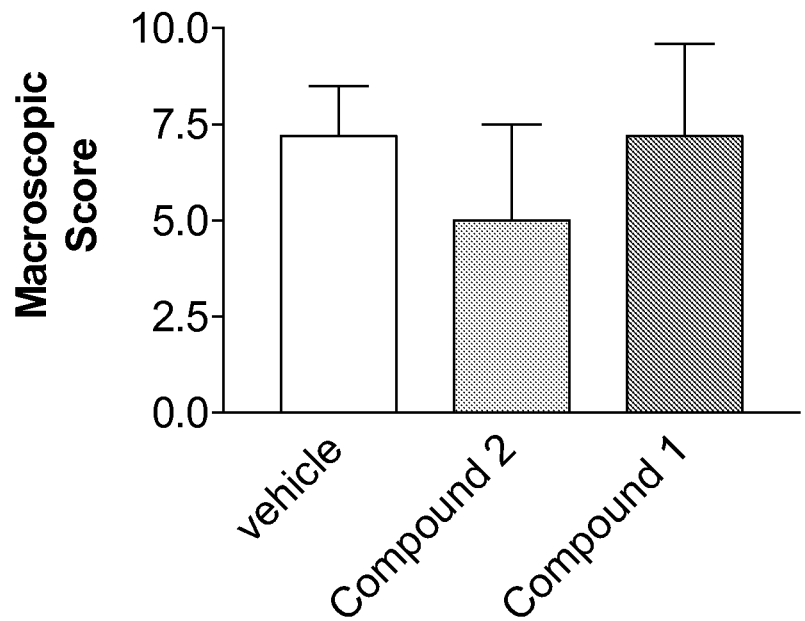

FIG. 12. Effects of Compound 1 and Compound 2 on colon histology in the TNBS-induced Crohn's Disease model. On Day 0, female Sprague-Dawley rats were administered TNBS using a stainless steel catheter that was inserted into the colon (8 cm proximal to the anus; 1.0 mL of solution containing 30 mg TNBS and 20% ethanol in PBS). On Days 0-5 animals received daily oral gavage of Vehicle (described in FIG. 7) or 50 mg/kg of Compound 1 or Compound 2 in Vehicle. On Day 6, the colons were removed, weighed and scored for macroscopic damage. The distal 6 cm were transected for subsequent histology and biochemical analyses. In this model, the macroscopic score is an index of histologic damage to the colon which increases as the disease progresses. The data demonstrate that Compound 2 reduces colon damage, whereas Compound 1 is much less active in this model.

Figure 13:
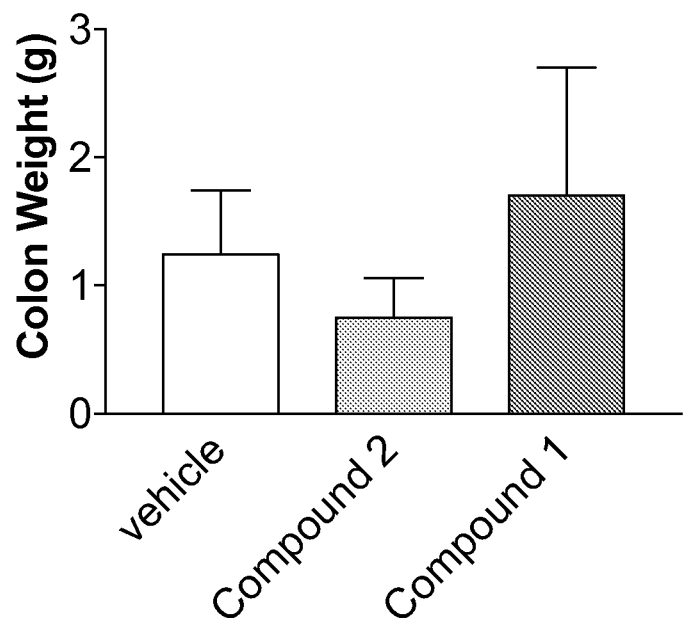

FIG. 13. Effects of Compound 1 and Compound 2 on colon weight in the TNBS-induced Crohn's Disease model. Colon weights were measured for the rats described in FIG. 12. Values represent the mean±std. dev. for 5-6 rats per group. In this model, colon weight increases as the disease progresses due to progressive inflammation-mediated edema. The data demonstrate that Compound 2 reduces colon edema, whereas Compound 1 is much less active in this model.

Figure 14:
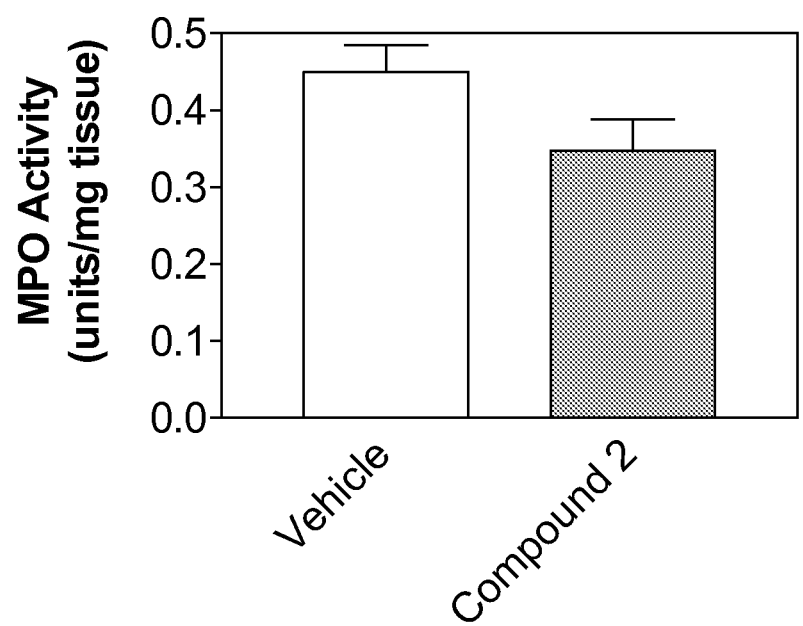

FIG. 14. Effects of Compound 2 on neutrophil infiltration into the colon in the TNBS-induced Crohn's Disease model. Neutrophil infiltration was evaluated in the rats described in FIG. 12. Values represent the mean±std. dev. for 5-6 rats per group. In this model, MPO activity in the colon increases as a result of neutrophil infiltration into the colon as the disease progresses. The data demonstrate that Compound 2 reduces neutrophil infiltration in this model.

DETAILED DESCRIPTION OF THE INVENTION

All patents and publications referred to herein are hereby incorporated by reference for all purposes.

Unless the substituents for a particular formula are expressly defined for that formula, they are understood to carry the definitions set forth in connection with the preceding formula to which the particular formula makes reference.

As noted above, the invention provides compounds of formula (I):

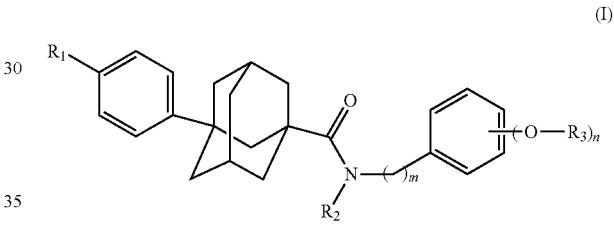

and pharmaceutically acceptable salts thereof, wherein
$R_1$ is H, Cl or F;
$R_2$ is H or alkyl;
m is 0, 1 or 2;
n is 1, 2, 3, 4 or 5;
each $R_3$ is independently H, —C(O)alkyl, —C(O)CH$_2$CH$_2$C(O)OH, $R_4$, —C(O)NR$_5$R$_6$, —O(O)(OR$_7$)$_2$ or glucosyl, provided that at least one $R_3$ is not H,
wherein
$R_4$ is a natural or unnatural amino acid linked through the carboxyl moiety as an ester,
$R_5$ is H or alkyl,
$R_6$ is H or alkyl, and
each $R_7$ is independently H or alkyl General terms for these compounds include alkyl esters, succinates, amino acid esters, carbamates, phosphates and glucosides.

Certain preferred compounds of formula (I) include compounds wherein $R_1$ is Cl. In other embodiments, $R_1$ is H; or $R_1$ is F.

In certain embodiments, compounds of formula (I) as described above have $R_2$=H. For example, one preferred embodiment compounds of formula (I) have $R_1$=Cl and $R_2$=H.

In certain embodiments, compounds of formula (I) as described above have m=1 or 2. For example, in one embodiment, m=1. In another embodiment, m=2. In certain embodiments, compounds of formula (I) as described above have n=1 or 2. For example, in one embodiment, n=1. In another embodiment, n=2. Certain preferred embodiments of compounds of formula (I) are those in which $R_1$ is Cl, $R_2$ is H, m is 1 or 2, and n is 1 or 2.

In certain embodiments of the compounds of formula (I) as described above, each $R_3$ is a —C(O)alkyl. For example, in certain embodiments, each $R_3$ is —C(O)CH$_3$.

In certain embodiments of the compounds of formula (I) as described above, each $R_3$ is a natural or unnatural amino acid. For example, in certain embodiments, each $R_3$ is a natural amino acid.

In certain embodiments of the compounds of formula (I) as described above, each $R_3$ is —C(O)CH$_2$CH$_2$C(O)OH.

In certain embodiments of the compounds of formula (I) as described above, each $R_3$ is —C(O)NR$_5$R$_6$.

In certain embodiments of the compounds of formula (I) as described above, each $R_3$ is —P(O)(OR$_7$)$_2$. In certain embodiments, both R7 are H. In other embodiments, both R7 are alkyl (e.g., unsubstituted lower alkyl).

In certain embodiments of the compounds of formula (I) as described above, each $R_3$ is glucosyl.

In certain embodiments of the compounds of formula (I) as described above, no $R_3$ is H. In certain embodiments of the compounds of formula (I) as described above, all $R_3$ are the same.

In certain embodiments of the compounds of formula (I) as described above, the

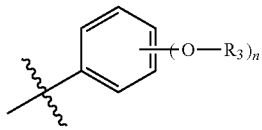

moiety is a catechol with substitution at least one catechol —OH. For example, in one embodiment, the

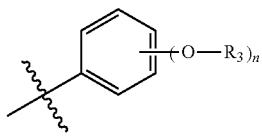

moiety has the structure

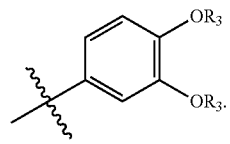

In one particularly preferred embodiment of the compounds of formula (I) as described above, the

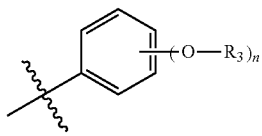

moiety has the structure

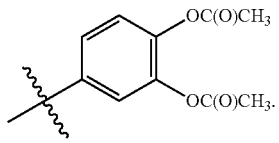

In one especially preferred embodiment of the invention, compounds of formula (I) have $R_1$=Cl, $R_2$=H, m=2, n=2, and each $R_3$=—C(O)alkyl, especially —C(O)CH$_3$.

For example, compounds of the invention include:
Acetic acid 2-acetoxy-5-(2-{[3-(4-chlorophenyl)-adamantane-1-carbonyl]-amino}ethyl)phenyl ester;
Propionic acid 2-propionyloxy-5-(2-{[3-(4-chlorophenyl)-adamantane-1-carbonyl]-amino}ethyl)phenyl ester;
Butyric acid 2-butyryloxy-5-(2-{[3-(4-chlorophenyl)-adamantane-1-carbonyl]-amino}ethyl)phenyl ester;
Isobutyric acid 5-(2-{[3-(4-chlorophenyl)adamantane-1-carbonyl]amino}ethyl)-2-hydroxyphenyl ester; and
2-Amino-3-methyl-butyric acid 5-(2-{[3-(4-chlorophenyl)adamantane-1-carbonyl]amino}ethyl)-2-hydroxyphenyl ester.

A particularly preferred compound of the present invention is acetic acid 2-acetoxy-5-(2-{[3-(4-chlorophenyl)-adamantane-1-carbonyl]-amino}ethyl)phenyl ester (Compound 2):

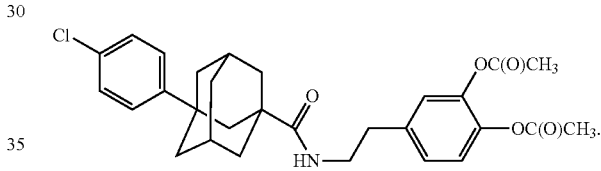

The invention also provides methods for treating a patient who has, or in preventing a patient from getting, a disease or condition selected from the group consisting of a hyperproliferative disease, an inflammatory disease, or an angiogenic disease, which includes administration of a therapeutically effective amount of a compound of formula (I) as described above or a pharmaceutically acceptable salt thereof, to a patient in need of such treatment or prevention. One preferred hyperproliferative disease which the compounds of the invention are useful in treating or preventing is cancer, including solid tumors such as head and neck cancers, lung cancers, gastrointestinal tract cancers, breast cancers, gynecologic cancers, testicular cancers, urinary tract cancers, neurological cancers, endocrine cancers, skin cancers, sarcomas, mediastinal cancers, retroperitoneal cancers, cardiovascular cancers, mastocytosis, carcinosarcomas, cylindroma, dental cancers, esthesioneuroblastoma, urachal cancer, Merkel cell carcinoma and paragangliomas, and hematopoietic cancers such as Hodgkin lymphoma, non-Hodgkin lymphoma, chronic leukemias, acute leukemias, myeloproliferative cancers, plasma cell dyscrasias, and myelodysplastic syndromes.

Other preferred diseases which can be treated or prevented with the compounds of the invention include inflammatory diseases, such as inflammatory bowel disease, arthritis, atherosclerosis, asthma, allergy, inflammatory kidney disease, circulatory shock, ischemia-reperfusion injury, post-surgical organ failure, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus.

Other preferred diseases which can be treated or prevented with the compounds of the invention include angiogenic diseases, such as diabetic retinopathy, arthritis, psoriasis, Kaposi's sarcoma, hemangiomas, myocardial angiogenesis, atherscelortic plaque neovascularization, and ocular angiogenic diseases such as choroidal neovascularization, retinopathy of prematurity (retrolental fibroplasias), macular degeneration, corneal graft rejection, rubeosis, neuroscular glacoma and Oster Webber syndrome.

The invention also provides pharmaceutical compositions that include a compound of formula (I) as described above or a pharmaceutically acceptable salt thereof, as active ingredient, in combination with a pharmaceutically acceptable carrier, medium, or auxiliary agent.

The pharmaceutical compositions of the present invention may be prepared in various forms for administration, including tablets, caplets, pills, or can be filled in suitable containers, such as capsules, or, in the case of suspensions, filled into bottles. As used herein "pharmaceutically acceptable carrier medium" includes any and all solvents, diluents, or other liquid vehicle; dispersion or suspension aids; surface active agents; preservatives; solid binders; lubricants and the like, as suited to the particular dosage form desired. Various vehicles and carriers used in formulating pharmaceutical compositions and known techniques for the preparation thereof are disclosed in *Remington's Pharmaceutical Sciences* (A. Osol et al. eds., 15th ed. 1975). Except insofar as any conventional carrier medium is incompatible with the chemical compounds of the present invention, such as by producing any undesirable biological effect or otherwise interacting in a deleterious manner with any other component of the pharmaceutical composition, the use of the carrier medium is contemplated to be within the scope of this invention.

In the pharmaceutical compositions of the present invention, the active agent may be present in an amount of at least 1% and not more than 99% by weight, based on the total weight of the composition, including carrier medium or auxiliary agents. Preferably, the proportion of active agent varies between 1% to 70% by weight of the composition. Pharmaceutical organic or inorganic solid or liquid carrier media suitable for enteral or parenteral administration can be used to make up the composition. Gelatin, lactose, starch, magnesium, stearate, talc, vegetable and animal fats and oils, gum polyalkylene glycol, or other known excipients or diluents for medicaments may all be suitable as carrier media.

The pharmaceutical compositions of the present invention may be administered using any amount and any route of administration effective for treating a patient who has, or in preventing a patient from getting, a disease or condition selected from the group consisting of a hyperproliferative disease, an inflammatory disease, and an angiogenic disease. Thus the expression "therapeutically effective amount," as used herein, refers to a sufficient amount of the active agent to provide the desired effect against target cells. The exact amount required will vary from subject to subject, depending on the species, age, and general condition of the subject; the particular compound; its mode of administration; and the like.

The pharmaceutical compounds of the present invention are preferably formulated in dosage unit form for ease of administration and uniformity of dosage. "Dosage unit form," as used herein, refers to a physically discrete unit of therapeutic agent appropriate for the animal to be treated. Each dosage should contain the quantity of active material calculated to produce the desired therapeutic effect either as such, or in association with the selected pharmaceutical carrier medium. Typically, the pharmaceutical composition will be administered in dosage units containing from about 0.1 mg to about 10,000 mg of the agent, with a range of about 1 mg to about 1000 mg being preferred.

The pharmaceutical compositions of the present invention may be administered orally or parenterally, such as by intramuscular injection, intraperitoneal injection, or intravenous infusion. The pharmaceutical compositions may be administered orally or parenterally at dosage levels of about 0.1 to about 1000 mg/kg, and preferably from about 1 to about 100 mg/kg, of animal body weight per day, one or more times a day, to obtain the desired therapeutic effect.

Although the pharmaceutical compositions of the present invention can be administered to any subject that can benefit from the therapeutic effects of the compositions, the compositions are intended particularly for the treatment of diseases in humans.

The pharmaceutical compositions of the present invention will typically be administered from 1 to 4 times a day, so as to deliver the daily dosage as described herein. Alternatively, dosages within these ranges can be administered by constant infusion over an extended period of time, usually 1 to 96 hours, until the desired therapeutic benefits have been obtained. However, the exact regimen for administration of the chemical compounds and pharmaceutical compositions described herein will necessarily be dependent on the needs of the animal being treated, the type of treatments being administered, and the judgment of the attending physician.

In certain situations, the compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Non-toxic pharmaceutically acceptable salts of the compounds of the present invention include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The invention provides compounds of formula (I) which are prodrugs of inhibitors of SK, and which are useful for modulating the sphingomyelin signal transduction pathway, and in treating and preventing hyperproliferative diseases, inflammatory diseases, and angiogenic diseases. The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Specific examples of methods of preparation can be found herein and in the art.

As discussed above, sphingolipids are critically important in regulating the balance between cell proliferation and apoptosis. Sphingosine 1-phosphate is produced by the enzyme SK and stimulates the proliferation of tumor cells. Concurrent depletion of ceramide by the action of SK blocks apoptosis. The compounds of the invention are prodrugs of inhibitors of human SK. Therefore, inhibition of SK activity according to the invention will attenuate tumor cell proliferation and promote apoptosis. Therefore, the compounds of the invention are useful as anticancer agents. Furthermore, since cell hyperproliferation is a required process in the development of atherosclerosis and psoriasis, the compounds of the invention, which are prodrugs of SK inhibitors, are useful in the treatment of these, and other, hyperproliferative diseases. Additionally, inappropriate activation and/or proliferation of specific classes of immune cells results in chronic inflammatory and autoimmune diseases. Consequently, compounds of the invention are also useful in the treatment of these diseases. Additionally, inappropriate angiogenesis results in a variety of diseases, as described below. Consequently, compounds of the invention are also useful in the treatment of these diseases.

DEFINITIONS

The definitions and explanations below are for the terms as used throughout this entire document, including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The symbol "-" in general represents a bond between two atoms in the chain. Thus $CH_3-O-CH_2-CH(R_t)-CH_3$ represents a 2-substituted-1-methoxypropane compound. In addition, the symbol "-" represents the point of attachment of the substituent to a compound. Thus for example aryl($C_1$-$C_6$) alkyl-indicates an alkylaryl group, such as benzyl, attached to the compound at the alkyl moiety.

Where multiple substituents are indicated as being attached to a structure, it is to be understood that the substituents can be the same or different.

The term "alkyl", as used herein alone or as part of a larger moiety, refers to a saturated aliphatic hydrocarbon including straight chain, branched chain or cyclic (also called "cycloalkyl") groups. Examples of alkyl groups include methyl, ethyl, propyl, isopropyl, butyl, iso-, sec- and tert-butyl, pentyl, hexyl, heptyl, 3-ethylbutyl, and the like. Preferably, the alkyl group has 1 to 20 carbon atoms (whenever a numerical range, e.g. "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms, for example an unsubstituted lower alkyl. The cycloalkyl can be monocyclic, or a polycyclic fused system. Examples of cycloalkyl groups include cyclopropyl, cyclobutyl, cyclolpentyl, cyclohexyl, cycloheptyl, cyclooctyl, and adamantyl. The alkyl or cycloalkyl group may be unsubstituted or substituted with 1, 2, 3 or more substituents. Examples of such substituents include, without limitation, halo, hydroxy, amino, alkoxy, alkylamino, dialkylamino, cycloalkyl, aryl, aryloxy, arylalkyloxy, heterocyclic radical, and (heterocyclic radical)oxy. Examples include fluoromethyl, hydroxyethyl, 2,3-dihydroxyethyl, (2- or 3-furanyl)methyl, cyclopropylmethyl, benzyloxyethyl, (3-pyridinyl)methyl, (2-thienyl)ethyl, hydroxypropyl, aminocyclohexyl, 2-dimethylaminobutyl, methoxymethyl, N-pyridinylethyl, and diethylaminoethyl.

The term "solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Exemplary solvates include ethanolates, methanolates, and the like. "Hydrate" is a solvate wherein the solvent is water.

Compounds that have the same molecular formula but differ in the nature or sequence of bonding of their atoms or arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, a carbon atom that is bonded to four different groups, a pair of enantiomers is possible. An enantiomer can be characterized by the absolute configuration of its asymmetric center and is described by the R- and S-sequencing rules of Cahn and Prelog, which are well known to those in the art. Additionally, enantiomers can be characterized by the manner in which a solution of the compound rotates a plane of polarized light and designated as dextrorotatory or levorotatory (i.e. as (+) or (−) isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless otherwise indicated, the specification and claims is intended to include both individual enantiomers as well as mixtures, racemic or otherwise, thereof.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention. Such compounds are useful, for example, as analytical tools or probes in biologic assays.

As used herein, "SK-related disorder", "SK-driven disorder", and "abnormal SK activity" all refer to a condition characterized by inappropriate, i.e., under or, more commonly, over, SK catalytic activity. Inappropriate catalytic activity can arise as the result of either: (1) SK expression in cells that normally do not express SK, (2) increased SK catalytic activity leading to unwanted cellular process, such as, without limitation, cell proliferation, gene regulation, resistance to apoptosis, and/or differentiation. Such changes in SK expression may occur by increased expression of SK and/or mutation of SK such that its catalytic activity is enhanced, (3) decreased SK catalytic activity leading to unwanted reductions in cellular processes. Some examples of SK-related disorders, without limitation, are described elsewhere in this application.

The term "method" refers to manners, means, techniques and procedures for accomplishing a given task including, but not limited to, those manners, means, techniques and procedures either known to, or readily developed from known manners, means, techniques and procedures by practitioners of the chemical, pharmaceutical, biological, biochemical and medical arts.

The term "modulation" or "modulating" refers to the alteration of the catalytic activity of SK. In particular, modulating refers to the activation or, preferably, inhibition of SK catalytic activity, depending on the concentration of the compound or salt to which SK is exposed.

The term "catalytic activity" as used herein refers to the rate of phosphorylation of sphingosine under the influence of SK.

The term "contacting" as used herein refers to bringing a compound of this invention and SK together in such a manner that the compound can affect the catalytic activity of SK, either directly, i.e., by interacting with SK itself, or indirectly, i.e., by altering the intracellular localization of SK. Such "contacting" can be accomplished in vitro, i.e. in a test tube, a Petri dish or the like. In a test tube, contacting may involve only a compound and SK or it may involve whole cells. Cells may also be maintained or grown in cell culture dishes and contacted with a compound in that environment. In this context, the ability of a particular compound to affect an SK-related disorder can be determined before the use of the compounds in vivo with more complex living organisms is attempted. For cells outside the organism, multiple methods exist, and are well-known to those skilled in the art, to allow contact of the compounds with SK including, but not limited to, direct cell microinjection and numerous techniques for promoting the movement of compounds across a biological membrane.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, mouse, rat, rabbit, bovine, equine, porcine, canine, feline, or primate.

The term "$IC_{50}$" or "50% inhibitory concentration" as used herein refers to the concentration of a compound that reduces a biological process by 50%. These processes can include, but are not limited to, enzymatic reactions, i.e. inhibition of SK catalytic activity, or cellular properties, e.g. cell proliferation, apoptosis or cellular production of S1P.

As used herein, "administer" or "administration" refers to the delivery of a compound or salt of the present invention or of a pharmaceutical composition containing a compound or salt of this invention to an organism for the purpose of prevention or treatment of an SK-related disorder.

As used herein, the terms "prevent", "preventing" and "prevention" refer to a method for barring an organism from acquiring an SK-related disorder.

As used herein, the terms "treat", "treating" and "treatment" refer to a method of alleviating or abrogating an SK-mediated disorder and/or its attendant symptoms.

The term "organism" refers to any living entity comprised of at least one cell. A living organism can be as simple as, for example, a single eukaryotic cell or as complex as a mammal. In a preferred aspect of this invention, the organism is a mammal. In a particularly preferred aspect of this invention, the mammal is a human being.

A "pharmaceutical composition" refers to a mixture of one or more of the compounds described herein, or pharmaceutically acceptable salts thereof, with other chemical components, such as physiologically acceptable carriers and excipients. The purpose of a pharmaceutical composition is to facilitate administration of a compound to an organism.

The term "pharmaceutically acceptable salt" refers to those salts that retain the biological effectiveness of the parent compound. Such salts include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid, or malonic acid and the like, preferably hydrochloric acid or (L)-malic acid; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, tromethamine, N-methylglucamine, and the like.

As used herein, the term a "physiologically acceptable carrier" refers to a carrier or diluent that does not cause significant irritation to an organism and does not abrogate the biological activity and properties of the administered compound. Typically, this includes those properties and/or substances that are acceptable to the patient from a pharmacological/toxicological point of view and to the manufacturing pharmaceutical chemist from a physical/chemical point of view regarding composition, formulation, stability, patient acceptance and bioavailability.

An "excipient" refers to an inert substance added to a pharmaceutical composition to further facilitate administration of a compound. Example, without limitations, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

The term "therapeutically effective amount" as used herein refers to that amount of the compound being administered that is effective to reduce or lessen at least one symptom of the disease being treated or to reduce or delay onset of one or more clinical markers or symptoms of the disease. In reference to the treatment of cancer, a therapeutically effective amount refers to that amount that has the effect of: (1) reducing the size of the tumor, (2) inhibiting, i.e. slowing to some extent, preferably stopping, tumor metastasis, (3) inhibiting, i.e. slowing to some extent, preferably stopping, tumor growth, and/or (4) relieving to some extent, preferably eliminating, one or more symptoms associated with the cancer.

The compounds of this invention act as prodrugs. The term "prodrug" refers to an agent which is converted into the parent drug in vivo. Prodrugs are often useful because, in some situations, they may be easier to administer than the parent drug. They may, for example, be bioavailable by oral administration whereas the parent drug is not. The prodrug may also have improved solubility in pharmaceutical compositions over the parent drug. Examples, without limitation, of a prodrug would be a compound of the present invention which is administered as an alkyl ester, succinate, amino acid ester, carbamate, phosphate or glucoside.

The compounds of this invention may also be metabolized by enzymes in the body of the organism, such as a human being, to generate a metabolite that can modulate the activity of SK.

Indications

Sphingosine kinase (SK), whose catalytic activity is modulated by metabolites of the compounds and compositions of this invention, is a key enzyme involved in signaling pathways that are abnormally activated in a variety of diseases. The following discussion outlines the roles of SK in hyperproliferative, inflammatory and angiogenic diseases, and consequently provides examples of uses of the compounds and compositions of this invention. The use of these compounds and compositions for the prevention and/or treatment of additional diseases in which SK is abnormally activated are also within the scope of the present invention.

Hyperproliferative Diseases.

The present invention relates to compounds, pharmaceutical compositions and methods useful for the treatment and/or prevention of hyperproliferative diseases. More specifically, the invention relates to compounds and pharmaceutical compositions whose metabolites inhibit the enzymatic activity of SK for the treatment and/or prevention of hyperproliferative diseases, such as cancer, psoriasis, mesangial cell proliferative disorders, atherosclerosis and restenosis. The following discussion demonstrates the role of SK in several of these hyperproliferative diseases. Since the same processes are involved in the above listed diseases, the compounds, pharmaceutical compositions and methods of this invention will be useful for the treatment and/or prevention of a variety of diseases.

Sphingosine-1-phosphate and ceramide have opposing effects on cancer cell proliferation and apoptosis. Sphingomyelin is not only a building block for cellular membranes but also serves as the precursor for potent lipid messengers that have profound cellular effects. Stimulus-induced metabolism of these lipids is critically involved in cancer cell biology. Consequently, these metabolic pathways offer targets for the development of new anticancer drugs.

Ceramide is produced by the hydrolysis of sphingomyelin in response to growth factors or other stimuli. Ceramide induces apoptosis in tumor cells, but can be further hydrolyzed by the action of ceramidase to produce sphingosine. Sphingosine is then rapidly phosphorylated by SK to produce S1P, which is a critical second messenger that exerts proliferative and antiapoptotic actions. A critical balance, i.e. a ceramide/S1P rheostat, has been hypothesized to determine the fate of the cell. In this model, the balance between the cellular concentrations of ceramide and S1P determines whether a cell proliferates or undergoes apoptosis. Upon exposure to mitogens or intracellular oncoproteins, the cells experience a rapid increase in the intracellular levels of S1P and depletion of ceramide levels. This situation promotes cell survival and proliferation. In contrast, activation of sphingomyelinase in the absence of activation of ceramidase and/or SK results in the accumulation of ceramide and subsequent apoptosis.

SK is the enzyme responsible for S1P production in cells. A variety of proliferative factors, including PKC activators, fetal calf serum and platelet-derived growth factor, EGF, and TNFα rapidly elevate cellular SK activity. S1P promotes signaling through the Ras-Raf-Mek-Erk pathway, setting up an amplification cascade for cell proliferation.

Sphingosine kinase and S1P play important roles in cancer pathogenesis. An oncogenic role of SK has been demonstrated Inhibition of SK by transfection with a dominant-negative SK mutant or by treatment of cells with the nonspecific SK inhibitor DMS blocks transformation mediated by oncogenic H-Ras. Because abnormal activation of Ras frequently occurs in cancer, these findings suggest a significant role of SK in this disease. SK has also been linked to estrogen signaling and estrogen-dependent tumorigenesis in MCF-7 cells. Other pathways or targets to which SK activity has been linked in hyperproliferative diseases include VEGF signaling, protein kinase C, TNFα, hepatocyte nuclear factor-1 and retinoic acid receptor alpha, intracellular calcium and caspase activation.

Cellular hyperproliferation is a characteristic of a variety of diseases, including, without limitation, cancer, psoriasis, mesangial cell proliferative disorders, atherosclerosis and restenosis. Therefore, the compounds, pharmaceutical compositions and methods of this invention will be useful for the prevention and/or treatment of cancer, including solid tumors, hematopoietic cancers and tumor metastases. Such cancers may include, without limitation, solid tumors such as head and neck cancers, lung cancers, gastrointestinal tract cancers, breast cancers, gynecologic cancers, testicular cancers, urinary tract cancers, neurological cancers, endocrine cancers, skin cancers, sarcomas, mediastinal cancers, retroperitoneal cancers, cardiovascular cancers, mastocytosis, carcinosarcomas, cylindroma, dental cancers, esthesioneuroblastoma, urachal cancer, Merkel cell carcinoma and paragangliomas. Additionally, such cancers may include, without limitation, hematopoietic cancers such as Hodgkin lymphoma, non-Hodgkin lymphoma, chronic leukemias, acute leukemias, myeloproliferative cancers, plasma cell dyscrasias, and myelodysplastic syndromes.

Psoriasis is a common chronic disfiguring skin disease that is characterized by well-demarcated, red, hardened and scaly plaques that may be limited or widespread. While the disease is rarely fatal, it has serious detrimental effects on the quality of life of the patient, and this is further complicated by the lack of effective therapies. There is therefore a large unmet need for effective and safe drugs for this condition. Psoriasis is characterized by local keratinocyte hyperproliferation, T cell-mediated inflammation and by localized angiogenesis. Abnormal activation of SK has been implicated in all of these processes. Therefore, SK inhibitors are expected to be of use in the therapy of psoriasis.

Mesangial cell hyperproliferative disorders refer to disorders brought about by the abnormal hyperproliferation of mesangial cells in the kidney. Mesangial hyperproliferative disorders include various human renal diseases such as glomerulonephritis, diabetic nephropathy, and malignant nephrosclerosis, as well as such disorders such as thrombotic microangiopathy syndromes, transplant rejection, and glomerulopathies. As the hyperproliferation of mesangial cells is induced by growth factors whose action is dependent on increased signaling through SK, the SK inhibitory compounds, pharmaceutical compositions and methods of this invention are expected to be of use in the therapy of these mesangial cell hyperproliferative disorders.

In addition to inflammatory processes discussed below, atherosclerosis and restenosis are characterized by hyperproliferation of vascular smooth muscle cells at the sites of the lesions. As the hyperproliferation of vascular smooth muscle cells is induced by growth factors whose action is dependent of increased signaling through SK, the SK inhibitory compounds, pharmaceutical compositions and methods of this invention are expected to be of use in the therapy of these vascular disorders.

Inflammatory Diseases.

The present invention also relates to compounds, pharmaceutical compositions and methods useful for the treatment and/or prevention of inflammatory diseases. More specifically, the invention relates to compounds and pharmaceutical compositions whose metabolites inhibit the enzymatic activity of SK for the treatment and/or prevention of inflammatory diseases, such as inflammatory bowel disease, arthritis, atherosclerosis, asthma, allergy, inflammatory kidney disease, circulatory shock, ischemia-reperfusion injury, post-surgical organ failure, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus. The following discussion demonstrates the role of SK in several of these inflammatory diseases. Since the same processes are involved in the above listed diseases, the compounds, pharmaceutical compositions and methods of this invention will be useful for the treatment and/or prevention of a variety of diseases.

Inflammatory bowel disease (IBD) encompasses a group of disorders characterized by pathological inflammation of the lower intestine. Crohn's disease and ulcerative colitis are the best-known forms of IBD, and are driven by infectious and immunologic mediators. From studies with animal models, it is clear that the full manifestations of IBD are dependent on synergy between the humoral and cellular immune responses. The notion that immune cells and cytokines play critical roles in the pathogenesis of IBD is well established. As discussed below, cytokines that promote inflammation in the intestine afflicted with IBD, activate a common mediator, SK. Most prominently, TNFα has been shown to play a significant role in IBD. TNFα activates several processes shown to contribute to IBD and is necessary for both the initiation and persistence of the Th1 response. For example, TNFα has been shown act through the induction of NFκB which has been implicated in increasing the proinflammatory enzymes nitric oxide synthase (NOS) and COX-2. COX-2 has been shown to play a key role in the inflammation of IBDs through its production of prostaglandins, and oxidative stress such as that mediated by nitric oxide produced by NOS has also shown to exacerbate IBD inflammation.

A common pathway of immune activation in IBDs is the local influx of mast cells, monocytes, macrophages and polymorphonuclear neutrophils which results in the secondary amplification of the inflammation process and produces the clinical manifestations of the diseases. This results in markedly increased numbers of mast cells in the mucosa of the ileum and colon of patients with IBD, which is accompanied by dramatic increases in TNFα. Additional mast cell secretory products, including histamine and tryptase, may be important in IBDs. Therefore, it is clear that inflammatory cascades play critical roles in the pathology of IBDs.

Ceramide is produced by the hydrolysis of sphingomyelin in response to inflammatory stresses, including TNFα, and can be hydrolyzed by ceramidase to produce sphingosine. Sphingosine is then rapidly phosphorylated by SK to produce S1P. Ceramidase and SK are also activated by cytokines and growth factors, leading to rapid increases in the intracellular levels of S1P and depletion of ceramide levels. This situation promotes cell proliferation and inhibits apoptosis. Deregulation of apoptosis in phagocytes is an important component of the chronic inflammatory state in IBDs, and S1P has been shown to protect neutrophils from apoptosis in response to Fas, TNFα and ceramide. Similarly, apoptosis of macrophages is blocked by S1P.

In addition to its role in regulating cell proliferation and apoptosis, S1P has been shown to have several important effects on cells that mediate immune functions. Platelets, monocytes and mast cells secrete S1P upon activation, promoting inflammatory cascades at the site of tissue damage. Activation of SK is required for the signaling responses, since the ability of TNFα to induce adhesion molecule expression via activation of NFκB is mimicked by S1P and is blocked by the SK inhibitor dimethylsphingosine. Similarly, S1P mimics the ability of TNFα to induce the expression of COX-2 and the synthesis of $PGE_2$, and knock-down of SK by RNA interference blocks these responses to TNFα but not S1P. S1P is also a mediator of $Ca^{2+}$ influx during neutrophil activation by TNFα and other stimuli, leading to the production of superoxide and other toxic radicals.

As the processes involved in IBDs are induced by cytokines and growth factors whose action is dependent on increased signaling through SK, the SK inhibitory compounds, pharmaceutical compositions and methods of this invention are expected to be of use in the therapy of IBDs.

Rheumatoid arthritis (RA) is a chronic, systemic disease that is characterized by synovial hyperplasia, massive cellular infiltration, erosion of the cartilage and bone, and an abnormal immune response. From studies in animal models, it is clear that the full manifestations of RA are dependent on synergy between the humoral and cellular immune responses. The notion that immune cells, especially neutrophils, and cytokines play critical roles in the pathogenesis of arthritis is well established.

The early phase of rheumatic inflammation is characterized by leukocyte infiltration into tissues, especially by neutrophils. In the case of RA, this occurs primarily in joints where leukocyte infiltration results in synovitis and synovium thickening producing the typical symptoms of warmth, redness, swelling and pain. As the disease progresses, the aberrant collection of cells invade and destroy the cartilage and bone within the joint leading to deformities and chronic pain. The inflammatory cytokines TNFα, IL-1β and IL-8 act as critical mediators of this infiltration, and these cytokines are present in the synovial fluid of patients with RA.

Leukocytes localize to sites of inflammatory injury as a result of the integrated actions of adhesion molecules, cytokines, and chemotactic factors. In lipopolysaccharide-induced arthritis in the rabbit, the production of TNFα and IL-1β in the initiative phase of inflammation paralleled the time course of leukocyte infiltration. The adherence of neutrophils to the vascular endothelium is a first step in the extravasation of cells into the interstitium. This process is mediated by selectins, integrins, and endothelial adhesion molecules, e.g. ICAM-1 and VCAM-1. Since TNFα induces the expression of ICAM-1 and VCAM-1 and is present in high concentrations in arthritic joints, it is likely that this protein plays a central role in the pathogenesis of the disease. This is supported by the clinical activity of anti-TNFα therapies such as Remicade. After adherence to the endothelium, leukocytes migrate along a chemoattractant concentration gradient. A further critical process in the progression of RA is the enhancement of the blood supply to the synovium through angiogenesis. Expression of the key angiogenic factor VEGF is potently induced by pro-inflammatory cytokines including TNFα. Together, these data point to important roles of TNFα, leukocytes, leukocyte adhesion molecules, leukocyte chemoattractants and angiogenesis in the pathogenesis of arthritic injury.

As the processes involved in arthritis are induced by cytokines and growth factors whose action is dependent on increased signaling through SK, the SK inhibitory compounds, pharmaceutical compositions and methods of this invention are expected to be of use in the prevention and/or therapy of arthritis.

Atherosclerosis is a complex vascular disease that involves a series of coordinated cellular and molecular events characteristic of inflammatory reactions. In response to vascular injury, the first atherosclerotic lesions are initiated by acute inflammatory reactions, mostly mediated by monocytes, platelets and T lymphocytes. These inflammatory cells are activated and recruited into the subendothelial vascular space through locally expressed chemotactic factors and adhesion molecules expressed on endothelial cell surface. Continuous recruitment of additional circulating inflammatory cells into the injured vascular wall potentiates the inflammatory reaction by further activating vascular smooth muscle (VSM) cell migration and proliferation. This chronic vascular inflammatory reaction leads to fibrous cap formation, which is an oxidant-rich inflammatory milieu composed of monocytes/macrophages and VSM cells. Over time, this fibrous cap can be destabilized and ruptured by extracellular metalloproteinases secreted by resident monocytes/macrophages. The ruptured fibrous cap can easily occlude vessels resulting in acute cardiac or cerebral ischemia. This underlying mechanism of atherosclerosis indicates that activation of monocyte/macrophage and VSM cell migration and proliferation play critical roles in the development and progression of atherosclerotic lesions. Importantly, it also suggests that a therapeutic approach that blocks the activities of these vascular inflammatory cells or smooth muscle cell proliferation should be able to prevent the progression and/or development of atherosclerosis.

SK is highly expressed in platelets allowing them to phosphorylate circulating sphingosine to produce S1P. In response to vessel injury, platelets release large amounts of S1P into the sites of injury which can exert mitogenic effects on VSM cells by activating S1P receptors. S1P is also produced in activated endothelial and VSM cells. In these cells, intracellularly produced S1P functions as a second messenger molecule, regulating $Ca^{2+}$ homeostasis associated with cell proliferation and suppression of apoptosis. Additionally, deregulation of apoptosis in phagocytes is an important component of the chronic inflammatory state of atherosclerosis, and S1P protects granulocytes from apoptosis. Together, these studies indicate that activation of SK alters sphingolipid metabolism in favor of S1P formation, resulting in pro-inflammatory and hyperproliferative cellular responses.

These studies indicate that SK is a new molecular target for atherosclerosis. The use of inhibitors of SK as anti-atherosclerosis agents will prevent the deleterious activation of leukocytes, as well as prevent infiltration and smooth muscle cell hyperproliferation, making the compounds, pharmaceutical compositions and methods of this invention useful for the treatment and/or prevention of atherosclerosis.

The physiological endpoint in asthma pathology is narrowing of the bronchial tubes due to inflammation. In a large portion of asthma cases, the inflammation is initiated and later amplified by exposure to allergens. Upon inhalation, these allergens, bind to circulating IgE and then bind to the high-affinity FcεRI surface receptors expressed by inflammatory cells residing in the bronchial mucosa. This extracellular binding leads to a cascade of signaling events inside the inflammatory cells, culminating in activation of these cells and secretion of multiple factors that trigger the cells lining the bronchial airways to swell, resulting in restricted bronchial tubes and decreased air exchange. The inflammation process in response to the initial exposure to allergen may not completely subside. Furthermore, additional exposures may lead to an exaggerated response called bronchial hyper-reactivity. This hyper-reactive state can lead to a permanent condition of restricted airways through airway remodeling. Consequently, unchecked inflammatory responses to initial allergen exposure may result in chronic inflammation and permanent bronchiolar constriction. Therefore, inhibiting or diminishing this exaggerated inflammation would likely decrease the symptoms associated with asthma.

Many studies have revealed the involvement of mast cells in the inflammatory process leading to asthma, and SK has been shown to be involved in allergen-stimulated mast cell activation, a critical step in the bronchial inflammatory process. In rat basophilic leukemia RBL-2H3 cells, IgE/Ag binding to the high-affinity FcεRI receptor leads to SK activation and conversion of sphingosine to S1P. The newly formed S1P increases intracellular calcium levels, which is necessary for mast cell activation. Alternately, high concentrations of sphingosine decrease IgE/Ag exposure-mediated leukotriene synthesis and diminish cytokine transcription and secretion.

In addition to the key role of SK and S1P in mast cell activation, S1P also has direct effects on downstream signaling in the asthma inflammation pathway. Increased S1P levels have been found in bronchoalveolar lavage fluid collected from asthmatic patients 24 hours after allergen challenge compared with non-asthmatic subjects. In conjunction with the finding that activated mast cells produce and secrete S1P, these results reveal a correlation between S1P and the asthmatic inflammatory response. Furthermore, airway smooth muscle (ASM) cells are responsive to S1P- and SK-dependent stimuli, such as TNFα and IL-1β. Furthermore, S1P treatment increases DNA synthesis, cell number and accelerated progression of ASM cells from $G_1$ to S phase.

In addition to the direct effects on ASM cells, S1P also regulates secretion of cytokines and expression of cell adhesion molecules that amplify the inflammatory response through leukocyte recruitment and facilitating extracellular component interaction. The multiple roles of S1P, and hence SK, in the bronchiolar inflammatory phase of asthma pathogenesis clearly indicate an opportunity for pharmacologic intervention in both the acute and chronic phases of this disease. The use of inhibitors of SK as anti-asthma agents will inhibit cytokine-mediated activation of leukocytes, thereby preventing the deleterious activation of leukocytes, as well as preventing airway smooth muscle cell hyperproliferation, making the compounds, pharmaceutical compositions and methods of this invention useful for the treatment and/or prevention of asthma.

Chronic obstructive pulmonary disease (COPD), like asthma, involves airflow obstruction and hyper-responsiveness that is associated with aberrant neutrophil activation in the lung tissue. This is clinically manifested as chronic bronchitis, fibrosis or emphysema, which together make up the fourth leading cause of death in the United States. Since activation of inflammatory cells by chemical insults in COPD occurs through NFκB-mediated pathways similar to those activated during asthma, it is likely that the compounds, pharmaceutical compositions and methods of this invention will also be useful for the treatment and/or prevention of COPD.

Ischemia-reperfusion injury is also associated with elevated levels of inflammatory cytokines that mediated their effects by pathways that require SK activity. For example, levels of TNFα are increased following ischemia-reperfusion, and this inflammatory response leads to organ failure. This situation arises acutely in patients undergoing many types of surgery where blood flow is temporarily halted to one or more tissues. Because of this etiology, it is likely that the compounds, pharmaceutical compositions and methods of this invention will also be useful for the treatment and/or prevention of ischemia-reperfusion injury, including damage to organs being used for transplantation.

Inflammation is also involved in a variety of skin disorders, including psoriasis, atopic dermatitis, contact sensitivity and acne, which affect more than 20% if the population. Although topical corticosteroids have been widely used, their adverse effects prevent long-term use. Since the inflammatory responses typically involve aberrant activation of signaling pathways detailed above, it is likely that the compounds, pharmaceutical compositions and methods of this invention will also be useful for the treatment of these skin diseases.

A variety of diseases including allergic encephalomyelitis, allergic neuritis, transplant allograft rejection, graft versus host disease, myocarditis, thyroiditis, nephritis, systemic lupus erthematosus, and insulin-dependent diabetes mellitus can be induced by inappropriate activation of T cells. Common features of the pathogenesis of these diseases include infiltration by mononuclear cells, expression of CD4 and CD8 autoreactive T cells, and hyperactive signaling by inflammatory mediators such as IL-1, IL-6 and TNFα. Since the inflammatory responses typically involve aberrant activation of signaling pathways detailed above, it is likely that the compounds, pharmaceutical compositions and methods of this invention will also be useful for the treatment of these T cell-mediated diseases of immunity.

Angiogenic Diseases.

The present invention also relates to compounds, pharmaceutical compositions and methods useful for the treatment and/or prevention of diseases that involve undesired angiogenesis. More specifically, the invention relates to the use of prodrug compounds and compositions that inhibit the enzymatic activity of SK for the treatment and/or prevention of angiogenic diseases, such as diabetic retinopathy, arthritis, cancer, psoriasis, Kaposi's sarcoma, hemangiomas, myocardial angiogenesis, atherosclerotic plaque neovascularization, and ocular angiogenic diseases such as choroidal neovascularization, retinopathy of prematurity (retrolental fibroplasias), macular degeneration, corneal graft rejection, rubeosis, neuroscular glacoma and Oster Webber syndrome. The following discussion demonstrates the role of SK in several of these angiogenic diseases. Since the same processes are involved in the above listed diseases, the compounds, pharmaceutical compositions and methods of this invention will be useful for the treatment and/or prevention of a variety of diseases.

Angiogenesis refers to the state in the body in which various growth factors or other stimuli promote the formation of new blood vessels. As discussed below, this process is critical to the pathology of a variety of diseases. In each case, excessive angiogenesis allows the progression of the disease and/or the produces undesired effects in the patient. Since conserved biochemical mechanisms regulate the proliferation of vascular endothelial cells that form these new blood vessels, i.e. neovascularization, identification of methods to inhibit these mechanisms are expected to have utility for the treatment and/or prevention of a variety of diseases. The following discussion provides further details in how the compounds, compositions and methods of the present invention can be used to inhibit angiogenesis in several of these diseases.

Diabetic retinopathy is a leading cause of vision impairment, and elevation in the expression of growth factors contributes to pathogenic angiogenesis in this disease. In particular, VEGF is a prominent contributor to the new vessel formation in the diabetic retina, and VEGF has been shown to be elevated in patients with proliferative diabetic retinopathy. In addition to diabetic retinopathy, several other debilitating ocular diseases, including age-related macular degeneration and choroidal neovascularization, are associated with excessive angiogenesis that is mediated by VEGF and other growth factors.

In the retina, VEGF is expressed in the pigmented epithelium, the neurosensory retina, the pericytes and the vascular smooth muscle layer. VEGF induces endothelial cell proliferation, favoring the formation of new vessels in the retina. At the same time, basic fibroblast growth factor (bFGF) in the retina is activated, and this factor acts in synergy with VEGF such that the two together induce the formation of new vessels in which the subendothelial matrix is much weaker than in normal vessels. Additionally, VEGF facilitates fluid extravasation in the interstitium, where exudates form in the retinal tissue. VEGF also promotes the fenestration of endothelial cells, a process that can give rise to intercellular channels through which fluids can leak, and disrupts tight junctions between cells. Thus, reduction of VEGF activity in the retina is likely to efficiently reduce the development and progression of retinal angiogenesis and vascular leakage which underlie the retinopathic process.

The pro-inflammatory cytokine TNFα has also been demonstrated to play a role in diabetic retinopathy since it alters the cytoskeleton of endothelial cells, resulting in leaky barrier function and endothelial cell activation. These changes in retinal endothelial cells are central in the pathologies of diabetic retinopathy.

A link between the actions of VEGF and SK may be involved in driving retinopathy. SK has been shown to mediate VEGF-induced activation of ras- and mitogen-activated protein kinases. VEGF has been shown to enhance intracellular signaling responses to S1P, thereby increasing its angiogenic actions. S1P has also been shown to stimulate NFκB activity leading to the production of COX-2, adhesion molecules and additional VEGF production, all of which have been linked to angiogenesis. Furthermore, the expression of the endothelial isoform of nitric oxide synthase (eNOS), a key signaling molecule in vascular endothelial cells and modulates a wide array of function including angiogenic responses, is regulated by SK. Clearly, SK is a central regulator of angiogenesis, supporting our hypothesis that its pharmacological manipulation may be therapeutically useful. S1P has also been shown to stimulate NFκB production which has been demonstrated to be angiogenic. NFκB leads to the production of COX-2, adhesion molecules and additional VEGF production, all of which have been linked to angiogenesis.

One of the most attractive sites of intervention in this pathway is the conversion of sphingosine to S1P by the enzyme SK. SK is the key enzyme responsible for the production of S1P synthesis in mammalian cells, which facilitates cell survival and proliferation, and mediates critical processes involved in angiogenesis and inflammation, including responses to VEGF and TNFα. Therefore, inhibition of S1P production is a potentially important point of therapeutic intervention for diabetic retinopathy.

The role of angiogenesis in cancer is well recognized. Growth of a tumor is dependent on neovascularization so that nutrients can be provided to the tumor cells. The major factor that promotes endothelial cell proliferation during tumor neovascularization is VEGF. As discussed above, signaling through VEGF receptors is dependent on the actions of SK. Therefore, the compounds, pharmaceutical compositions and methods of this invention will have utility for the treatment of cancer.

More than 50 eye diseases have been linked to the stimulation of choroidal neovascularization, although the three main diseases that cause this pathology are age-related macular degeneration, myopia and ocular trauma. Even though most of these causes are idiopathic, among the known causes are related to degeneration, infections, choroidal tumors and or trauma. Among soft contact lens wearers, choroidal neovascularization can be caused by the lack of oxygen to the eyeball. As the choroidal neovascularization is induced by growth factors whose action is dependent on increased signaling through SK, the SK inhibitory prodrugs, pharmaceutical compositions and methods of this invention are expected to be of use in the therapy of disorders of choroidal neovascularization.

Hemangiomas are angiogenic diseases characterized by the proliferation of capillary endothelium with accumulation of mast cells, fibroblasts and macrophages. They represent the most frequent tumors of infancy, and are characterized by rapid neonatal growth (proliferating phase). By the age of 6 to 10 months, the hemangioma's growth rate becomes proportional to the growth rate of the child, followed by a very slow regression for the next 5 to 8 years (involuting phase). Most hemangiomas occur as single tumors, whereas about 20% of the affected infants have multiple tumors, which may appear at any body site. Several studies have provided insight into the histopathology of these lesions. In particular, proliferating hemangiomas express high levels of proliferating cell nuclear antigen (a marker for cells in the S phase), type IV collagenase, VEGF and FGF-2. As the hemangiomas are induced by growth factors whose action is dependent on increased signaling through SK, the SK inhibitory compounds, pharmaceutical compositions and methods of this invention are expected to be of use in the therapy of hemangiomas.

Psoriasis and Kaposi's sarcoma are angiogenic and proliferative disorders of the skin. Hypervascular psoriatic lesions express high levels of the angiogenic inducer IL-8, whereas the expression of the endogenous inhibitor TSP-1 is decreased. Kaposi's sarcoma (KS) is the most common tumor associated with human immunodeficiency virus (HIV) infection and is in this setting almost always associated with infection by human herpes virus 8. Typical features of KS are proliferating spindle-shaped cells, considered to be the tumor cells and endothelial cells forming blood vessels. KS is a cytokine-mediated disease, highly responsive to different inflammatory mediators like IL-1β, TNF-α and IFN-γ and angiogenic factors. As the progression of psoriasis and KS are induced by growth factors whose action is dependent on increased signaling through SK, the SK inhibitory compounds, pharmaceutical compositions and methods of this invention are expected to be of use in the therapy of these disorders.

EXAMPLES

The present invention may be better understood with reference to the following examples. These examples are intended to be representative of specific embodiments of the invention, and are not intended as limiting the scope of the invention.

Representative compounds of the invention include those in Table 1. Structures were named using Chemdraw Ultra, version 7.0.1, available from CambridgeSoft Corporation, 100 CambridgePark Drive, Cambridge, Mass. 02140, USA.

TABLE 1

Representative compounds of the invention.

| Cmpd | Chemical name | $R_1$ | $R_2$ | $R_3$ | m | n |
|---|---|---|---|---|---|---|
| 1 | 3-(4-Chlorophenyl)-adamantane-1-carboxylic acid [2-(3,4-dihydroxyphenyl)-ethyl]amide | Cl | H | 3-H 4-H | 2 | 2 |
| 2 | Acetic acid 2-acetoxy-5-(2-{[3-(4-chlorophenyl)-adamantane-1-carbonyl]-amino}ethyl)phenyl ester (Acetyl diester of Compound 1) | Cl | H | 3-C(O)CH$_3$ 4-C(O)CH$_3$ | 2 | 2 |
| 3 | Propionic acid 2-propionyloxy-5-(2-{[3-(4-chlorophenyl)-adamantane-1-carbonyl]-amino}ethyl)phenyl ester (Propionyl diester of Compound 1) | Cl | H | 3-C(O)CH$_2$CH$_3$ 4-C(O)CH$_2$CH$_3$ | 2 | 2 |
| 4 | Butyric acid 2-butyryloxy-5-(2-{[3-(4-chlorophenyl)-adamantane-1-carbonyl]-amino}ethyl)phenyl ester (Butyl diester of Compound 1) | Cl | H | 3-C(O)CH$_2$CH$_2$CH$_3$ 4-C(O)CH$_2$CH$_2$CH$_3$ | 2 | 2 |
| 5 | Isobutyric acid 5-(2-{[3-(4-chlorophenyl)adamantane-1-carbonyl]amino}ethyl)-2-hydroxyphenyl ester (Isobutyl monoester of Compound 1) | Cl | H | 3-C(O)CH(CH$_3$)$_2$ 4-OH | 2 | 2 |
| 6 | 2-Amino-3-methyl-butyric acid 5-(2-{[3-(4-chlorophenyl)adamantane-1-carbonyl]amino}ethyl)-2-hydroxyphenyl ester (Valine monoester of Compound 1) | Cl | H | 3-valine 4-OH | 2 | 2 |

General Methods.

NMR spectra were obtained on Varian 500 and Bruker 500 instruments in CDCl$_3$, DMSO-d$_6$. Chemical shifts are quoted relative to TMS for $^1$H- and $^{13}$C-NMR spectra. LC/MS analyses were conducted using a Finnigan LCQ Classic LC/MS/MS spectrometer, and MALDI-TOF MS Spectra were obtained on a Voyager RP mass spectrometer. Solvents were dried and distilled prior to use. Reactions requiring anhydrous conditions were conducted under an atmosphere of nitrogen and column chromatography was carried out over silica gel (Merck, silica gel 60, 230-400 mesh). Reagents and commercially available materials were used without further purification.

Example 1

Method for the Synthesis of 3-(4-chlorophenyl)adamantane-1-carboxylic acid [2-(3,4-dihydroxyphenyl)ethyl]amide: Compound 1

The general synthetic approach involved the bromination of adamantane-1-carboxylic acid (1) in the presence of aluminum chloride (AlCl$_3$) to give intermediate (2) which was converted to intermediate (3) by a Friedel-Crafts reaction in the presence of FeCl$_3$. Intermediate 3 was reacted with thionyl chloride (SOCl$_2$) to give intermediate (4). By reaction of intermediate 4 with 3-hydroxytyramine hydrochloride (5) in DMF, Compound 1 was obtained.

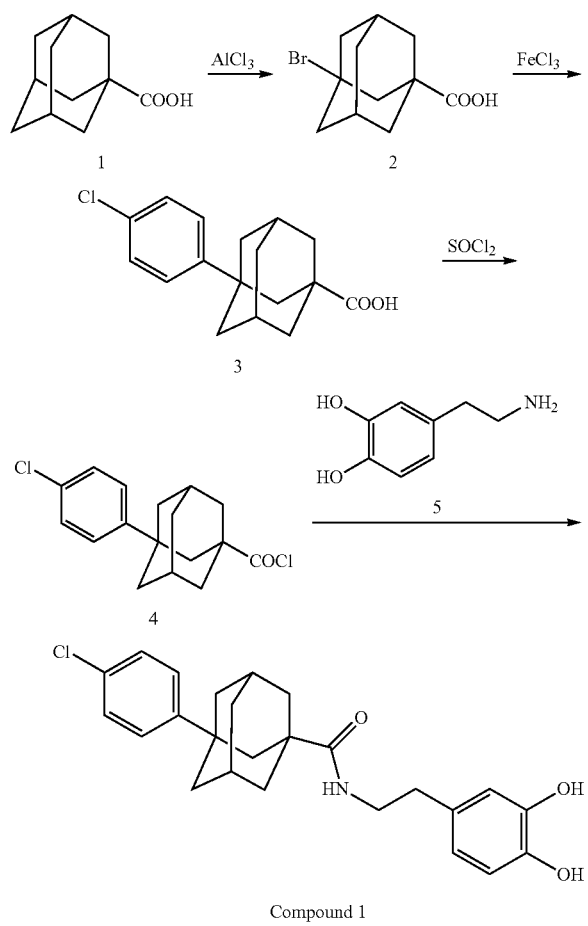

Compound 1 under $N_2$, and the mixture was stirred at 60° C. for 24 hr and then cool to room temperature. The mixture was evaporated under a vacuum, and 10% HCL was slowly added to the mixture until it reached a pH value of 1. The mixture was then extracted with 20 mL $CHCl_3$, washed three times with water (10 mL each), dried with anhydrous $Na_2SO_4$, filtered and concentrated to give Compound 1 as white crystals (yield=83%) with a melting point of 146-148° C. $^1$H NMR (500 MHz, DMSO) δ 1.63-1.68 (m, 2H, Admant-H), 1.71-1.83 (m, 10H, Admant-H), 2.14 (s, 2H, Admant-H), 2.50-2.53 (m, 2H, $CH_2$), 3.15-3.18 (t, J=7.5 Hz, 2H, $NCH_2$), 3.40 (s, 1H, NH), 6.40-6.42 (d, J=10 Hz, 1H, Ar—H), 6.56 (s, 1H, Ar—H), 6.62-6.63 (d, J=5 Hz, 1H, Ar—H), 7.36-7.41 (m, 4H, Ar—H), 8.68 (s(br), 2H, OH). $^{13}$C NMR (500 MHz, DMSO) δ 28.8, 31.3, 35.0, 35.5, 36.3, 36.6, 38.3, 41.0, 41.3, 42.0, 44.3, 115.8, 116.4, 119.8, 127.4, 128.5, 130.7, 131.0, 149.6, 162.9, 176.8. Mass spectroscopy m/z (relative intensity) 426.18 ($MH^+$, 100), 427.18 (68), 428.18 (75).

Example 2

Method for the Synthesis of acetic acid 2-acetoxy-4-(2-{[3-(4-chlorophenyl)adamantane-1-carbonyl]amino}ethyl)phenyl ester: Compound 2

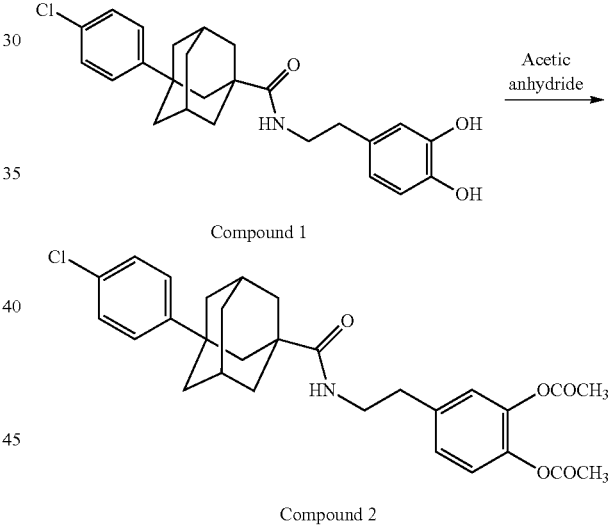

Compound 2

More specifically, adamantane-1-carboxylic acid (1) (45 g, 0.25 mol) was added to a mixture of $AlCl_3$ (45 g, 0.34 mol) and $Br_2$ (450 g) at 0° C. and stirred at 0-10° C. for 48 hrs, and then kept for 5 hrs at about 20° C. The mixture was then poured onto 500 g crushed ice, diluted with 300 mL of $CHCl_3$ and decolorized with solid $Na_2S_2O_5$. The aqueous phase was extracted twice with $Et_2O$ (50 mL each), and the combined organic phases were washed with $H_2O$ and extracted with 10% NaOH. The alkaline extraction was acidified with $2NH_2SO_4$ and kept overnight to provide 49 g (yield=75.7%) of 3-bromoadamantane-1-carboxylic acid (2). Over a course of 0.5 hr, intermediate 2 (16.0 g, 61.7 mmol) in 50 mL of dry chlorobenzene was added at −10° C. to 100 mL of dry chlorobenzene containing 9.3 g (70 mmol) of $AlCl_3$. The mixture was then warmed to room temperature for 1 hr, and then heated to 90° C. for 10 hr. The mixture was then poured onto 200 g of crushed ice and filtered to provide 14.2 g (yield=79.3%) of 3-(4-chlorophenyl)adamantane-1-carboxylic acid (3). Intermediate 3 (1 mmol) was added to a 50 mL round-bottom flask containing HPLC-grade toluene (20 mL), fitted with reflux condenser, and dry $N_2$ was introduced. The mixture was stirred while thionyl chloride ($SOCl_2$) (10 mmol) was added, and refluxed for 1 hr. The sample was then evaporated under a vacuum to produce intermediate 4,3-(4-chlorophenyl)adamantane-1-carbonyl chloride. Without further purification, intermediate 4 was added to 5 mL of a mixture containing 3-hydroxytyramine hydrochloride (5, 1 mmol), NaOH (1 mmol) and $Na_2CO_3$ (1 mmol) in 5 mL DMF Compound 1 (1 g) was dissolved in 10 mL of acetic anhydride with a catalytic amount of 98% $H_2SO_4$ and stirred under $N_2$ for 3 days at room temperature. The solution was then concentrated under a vacuum and filtered to give the product Compound 2 (yield=54%), with a melting point of 160-162° C. $^1$H NMR (500 MHz, $CDCl_3$) δ 1.74 (m, 2H, Admant-H), 1.81-1.88 (m, 8H, Admant-H), 1.93 (s, 2H, Admant-H), 2.26-2.27 (m, 2H, Admant-H), 2.28 (s, 3H, $COCH_3$), 2.31 (s, 3H, $COCH_3$), 2.83-2.85 (t, J=5 Hz, 2H, $CH_2$), 3.50-3.54 (q, 2H, $NCH_2$), 5.69 (s, 1H, NH), 7.01-7.02 (d, J=5 Hz, 1H, Ar—H), 7.07-7.09 (d, d, 1H, H—Ar), 7.13-7.15 (d, J=10 Hz, 1H, Ar—H), 7.30 (s, 4H, Ar—H). $^{13}$C NMR (500 MHz, $CDCl_3$) δ 20.6, 20.7, 28.8, 35.0, 35.5, 36.5, 38.3, 40.2, 40.3, 41.7, 42.0, 44.5, 123.5, 124.0, 126.4, 127.0, 128.3, 131.5, 138.0, 140.6, 142.0, 148.4, 168.4, 168.5, 177.5. Mass spectroscopy m/z (relative intensity) 510.24 ($M^+$, 100), 511.24 (38), 512.24 (45).

It will be recognized by those practicing the art that varying the conditions of this reaction will allow the synthesis of diesters and monoesters, i.e. modification of the 3- and/or 4-hydroxyl moieties of Compound 1, which can be isolated by a variety of chromatographic or crystallographic techniques.

Example 3

Method for the Synthesis of propionic acid 2-propionyloxy-5-(2-{[3-(4-chlorophenyl)adamantane-1-carbonyl]amino}ethyl)phenyl ester: Compound 3

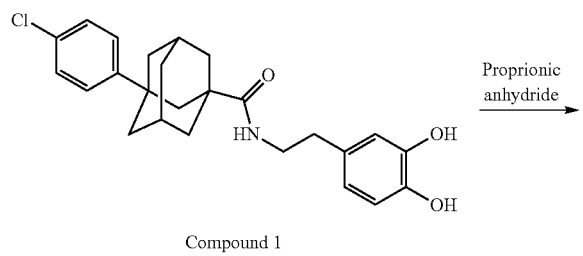

Compound 1

Proprionic anhydride →

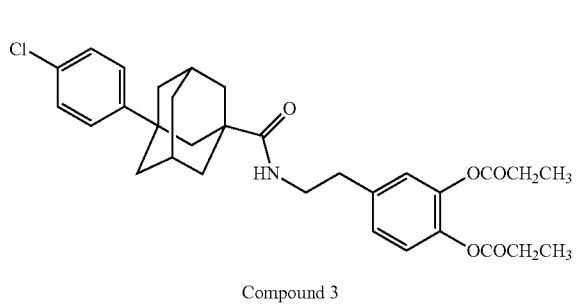

Compound 3

Compound 1 was dissolved in propionic anhydride with a catalytic amount of 98% $H_2SO_4$ and stirred under $N_2$ for 3 days at room temperature. The solution was then concentrated under a vacuum and filtered to give the product Compound 3, with a melting point of 114-115° C. $^1$H NMR (500 MHz, $CDCl_3$) δ 1.24-1.30 (m, 6H, $2CH_3$), 1.74 (m, 2H, Admant-H), 1.84-1.87 (m, 8H, Admant-H), 1.93 (s, 2H, Admant-H), 2.26 (m, 2H, Admant-H), 2.53-2.61 (m, 4H, $2COCH_2$), 2.82-2.85 (t, J=7.5 Hz, 2H, $CH_2$), 3.50-3.54 (q, 2H, $NCH_2$), 5.40 (s, 1H, NH), 7.01-7.02 (d, J=5 Hz, 1H, Ar—H), 7.06-7.08 (d, d, 1H, H—Ar), 7.13-7.15 (d, J=10 Hz, 1H, Ar—H), 7.30 (s, 4H, Ar—H); $^{13}$C NMR (500 MHz, $CDCl_3$) δ 9.1, 27.5, 28.8, 35.0, 35.5, 36.5, 38.3, 40.3, 41.7, 42.0, 44.5, 123.5, 123.9, 126.4, 126.8, 128.3, 131.5, 137.8, 140.7, 142.1, 148.4, 171.7, 171.8, 177.4; MS m/z (relative intensity) 538.61 ($MH^+$, 100), 539.61 (38), 540.61 (45).

It will be recognized by those practicing the art that varying the conditions of this reaction will allow the synthesis of diesters and monoesters, i.e. modification of the 3- and/or 4-hydroxyl moieties of Compound 1, which can be isolated by a variety of chromatographic or crystallographic techniques.

Example 4

Method for the Synthesis of butyric acid 2-butyryloxy-5-(2-{[3-(4-chlorophenyl)adamantane-1-carbonyl]amino}ethyl)phenyl ester: Compound 4

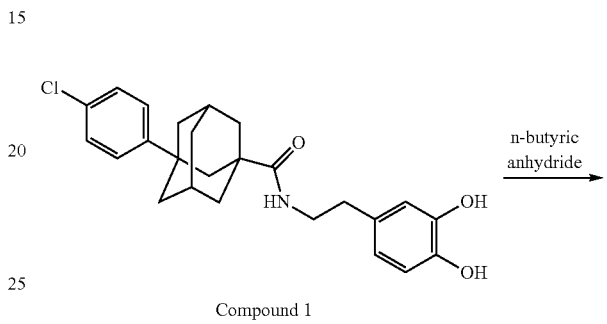

Compound 1 n-butyric anhydride →

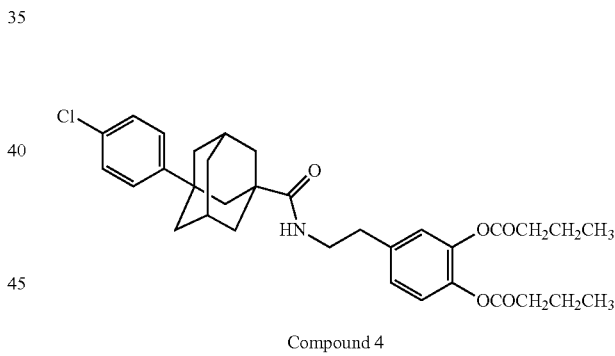

Compound 4

Compound 1 was dissolved in n-butyric anhydride with a catalytic amount of 98% $H_2SO_4$ and stirred under $N_2$ for 3 days at room temperature. The solution was then concentrated under a vacuum and filtered to give the product Compound 4, with a melting point of 78-80° C. $^1$H NMR (500 MHz, $CDCl_3$) δ 1.03-1.08 (m, 6H, $2CH_3$), 1.74 (m, 2H, Admant-H), 1.75-1.87 (m, 12H, $2CH_2$, Admant-H), 1.93 (s, 2H, Admant-H), 2.26 (m, 2H, Admant-H), 2.49-2.55 (m, 4H, $2COCH_2$), 2.82-2.85 (t, J=7.5 Hz, 2H, $CH_2$), 3.50-3.54 (q, 2H, $NCH_2$), 5.69 (s, 1H, NH), 7.01-7.02 (d, J=5 Hz, 1H, Ar—H), 7.06-7.08 (d, d, 1H, H—Ar), 7.12-7.14 (d, J=10 Hz, 1H, Ar—H), 7.30 (s, 4H, Ar—H); MS m/z (relative intensity) 566.73 ($MH^+$, 50), 567.61 (12), 568.60 (20).

It will be recognized by those practicing the art that varying the conditions of this reaction will allow the synthesis of diesters and monoesters, i.e. modification of the 3- and/or 4-hydroxyl moieties of Compound 1, which can be isolated by a variety of chromatographic or crystallographic techniques.

Example 5

Method for the Synthesis of isobutyric acid 5-(2-{[3-(4-chlorophenyl)adamantane-1-carbonyl]amino}ethyl)-2-hydroxyphenyl ester: Compound 5

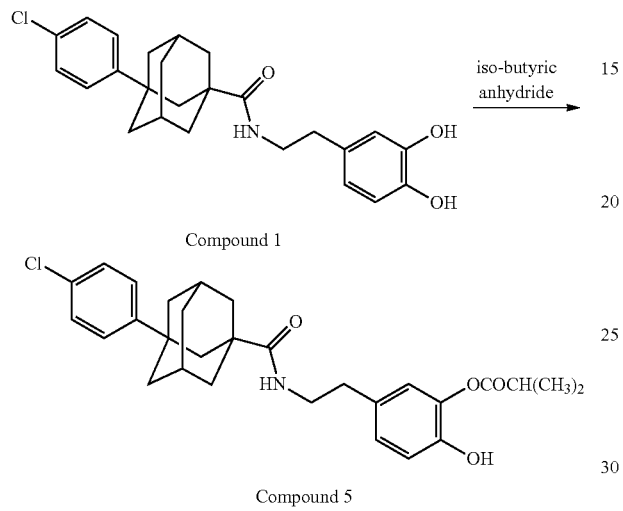

Compound 1 was dissolved in iso-butyric anhydride with a catalytic amount of 98% $H_2SO_4$ and stirred under $N_2$ for 3 days at room temperature. The solution was then concentrated under a vacuum and filtered to give the product Compound 5, with a melting point of 126-128° C. $^1$H NMR (500 MHz, $CDCl_3$) δ 1.29-1.33 (d, d, 6H, $2CH_3$), 1.74 (m, 2H, Admant-H), 1.81-1.88 (m, 8H, Admant-H), 1.94 (s, 2H, Admant-H), 2.26 (m, 2H, Admant-H), 2.74-2.81 (m, 2H, 2COCH), 2.82-2.85 (t, J=7.5 Hz, 2H, $CH_2$), 3.50-3.54 (q, 2H, $NCH_2$), 5.68 (s, 1H, NH), 6.99 (s, 1H, Ar—H), 7.05-7.07 (d, d, 1H, H—Ar), 7.11-7.13 (d, J=10 Hz, 1H, Ar—H), 7.30 (s, 4H, Ar—H); $^{13}$C NMR (500 MHz, $CDCl_3$) δ 18.9, 28.8, 34.0, 35.0, 35.5, 36.5, 38.3, 40.3, 41.7, 42.0, 44.4, 123.5, 123.9, 126.4, 126.7, 128.3, 131.5, 137.7, 140.9, 142.2, 148.4, 174.4, 174.5, 177.4; MS m/z (relative intensity) 566.22 ($MH^+$, 50), 567.22 (10), 567.22 (15).

It will be recognized by those practicing the art that varying the conditions of this reaction will allow the synthesis of diesters and monoesters, i.e. modification of the 3- and/or 4-hydroxyl moieties of Compound 1, which can be isolated by a variety of chromatographic or crystallographic techniques.

Example 6

Method for the Synthesis of Additional Alkyl Esters of Compound 1

As demonstrated in Examples 1-5, reaction of Compound 1 with a variety of alkyl anhydrides results in the generation of mono- or di-esters. Therefore, additional esters of Compound 1 can be prepared by reacting the appropriate anhydride with Compound 1 under slightly acidic conditions. Other methods for the preparation of organic esters are well known in the art, and can be used for the synthesis of these and further alkyl esters of Compound 1. For example, Compound 1 can be reacted with acyl chlorides of the desired alkyl substitution. These additional esters are therefore subjects of the present invention.

It will be recognized by those practicing the art that varying the conditions of this reaction will allow the synthesis of diesters and monoesters, i.e. modification of the 3- and/or 4-hydroxyl moieties of Compound 1, which can be isolated by a variety of chromatographic or crystallographic techniques.

Example 7

Method for the Synthesis of Amino Acid-Esters of Compound 1

Amino acid ester prodrugs are frequently actively transported by carriers in the gastrointestinal tract, and consequently can improve the oral absorption of drugs. Amino acid esters of Compound 1 can be prepared by coupling an amino-protected amino acid with Compound 1 using a variety of strategies. As one example, the valine ester of Compound 1, i.e. Compound 6 was prepared as follows:

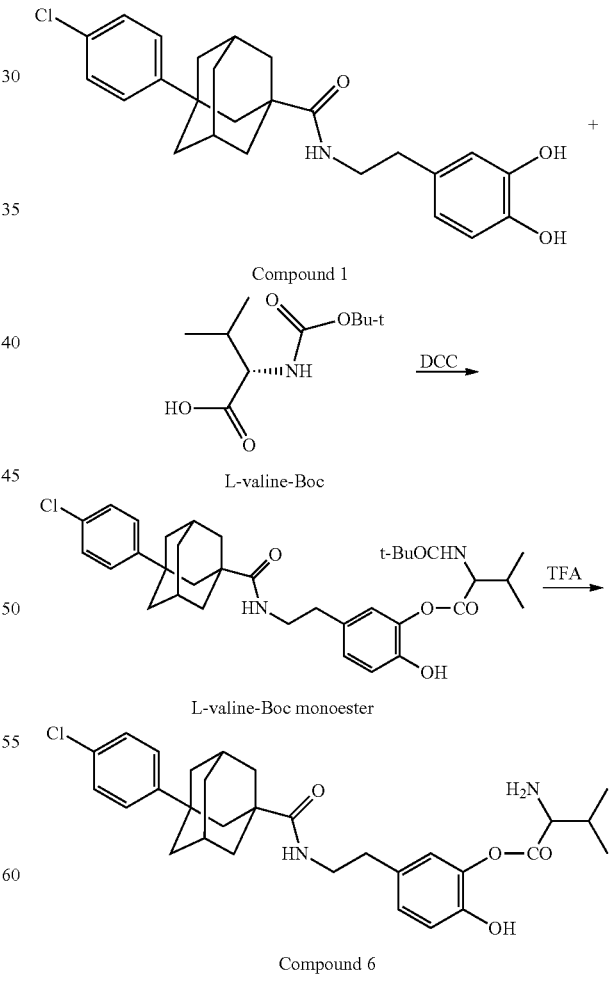

Compound 1 was reacted with commercially-available L-Valine-Boc using DCC as the coupling reagent, producing the intermediate L-Valine-Boc ester. Treatment of this intermediate with trifluoroacetic acid (TFA) in dichloromethane at 0° C. provided Compound 6.: $^1$H NMR (500 MHz, CDCl$_3$) δ 1.20-1.30 (m, 7H, CH(CH$_3$)$_2$), 1.74 (m, 2H, Admant-H), 1.84-1.87 (m, 8H, Admant-H), 1.98-1.99 (d, J=5 Hz, 2H, Admant-H), 2.20 (m, 2H, Admant-H), 2.61-2.63 (m, 2H, NH$_2$), 2.72-2.76 (m, 2H, CH$_2$), 3.41-3.46 (q, 2H, NCH$_2$), 4.44-4.46 (t, J=5 Hz, 1H, COCH), 5.12-5.14 (m, 1H, NH), 6.69-6.70 (d, J=5 Hz, 1H, Ar—H), 6.89-7.0 (m, 2H, H—Ar), 7.33-7.35 (d, J=10 Hz, 2H, Ar—H), 7.40-7.42 (d, J=10 Hz, 2H, Ar—H), 8.04 (s, 1H, OH); MS m/z (relative intensity) 525.23 (MH$^+$, 30), 526.23 (10), 527.23 (15).

It will be recognized by those practicing the art that varying the conditions of this reaction will allow the synthesis of amino acid diesters and monoesters, i.e. modification of the 3- and/or 4-hydroxyl moieties of Compound 1, which can be isolated by a variety of chromatographic or crystallographic techniques.

Example 8

Method for the Synthesis of Succinate Esters of Compound 1

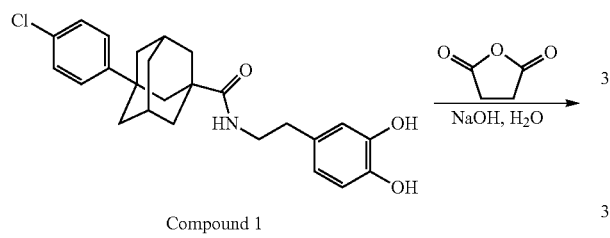

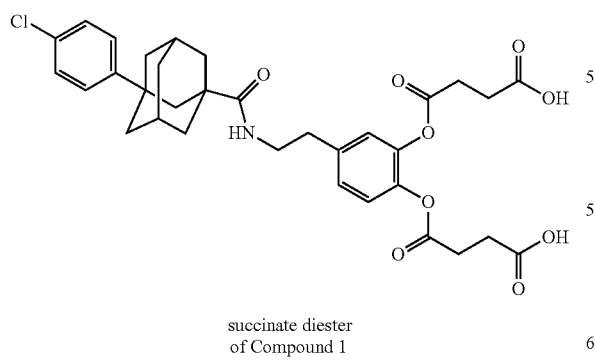

succinate diester
of Compound 1

Compound 1 can be reacted with succinic anhydride under basic conditions to yield the succinate diester of Compound 1. It will be recognized by those practicing the art that varying the conditions of this reaction will allow the synthesis of succinate diesters and monoesters, i.e. modification of the 3- and/or 4-hydroxyl moieties of Compound 1, which can be isolated by a variety of chromatographic or crystallographic techniques.

Example 9

Method for the Synthesis of Phosphate-Esters of Compound 1

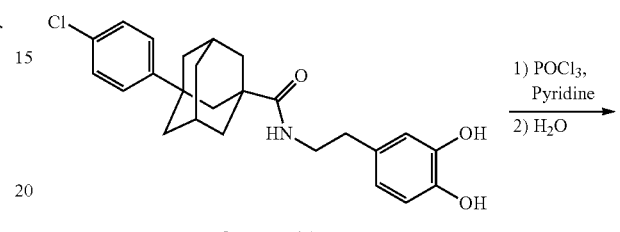

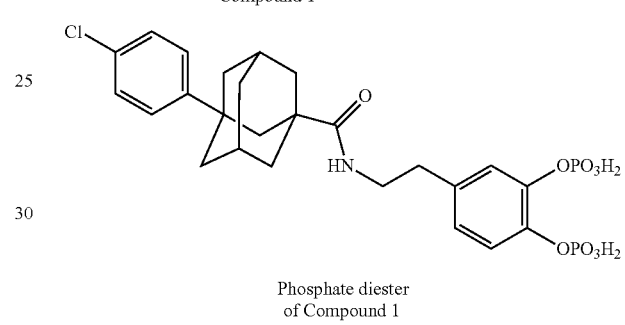

Phosphate diester
of Compound 1

Compound 1 can be reacted with phosphorous oxychloride under basic conditions, followed by hydrolysis in water, to yield the phosphate diester of Compound 1. It will be recognized by those practicing the art that varying the conditions of this reaction will allow the synthesis of phosphate diesters and monoesters, i.e. modification of the 3- and/or 4-hydroxyl moieties of Compound 1, which can be isolated by a variety of chromatographic or crystallographic techniques. Reaction of Compound 1 with different phosphoric acid chlorides, such as dimethyl phosphorochloridate, can provide alkyl-substituted phosphate esters.

Example 10

Method for the Synthesis of Carbamates of Compound 1

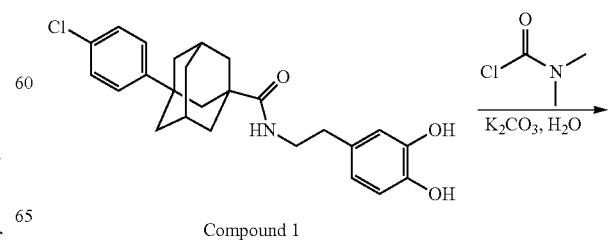

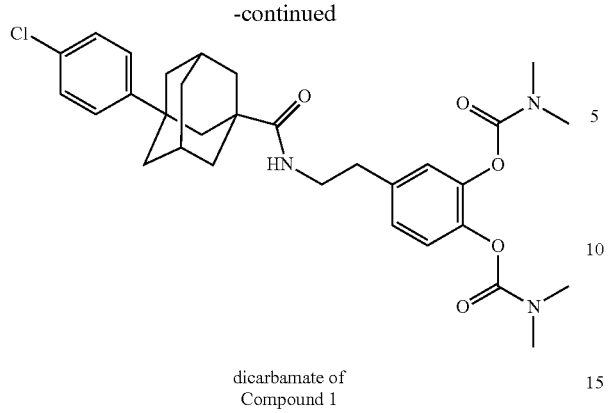

dicarbamate of
Compound 1

Compound 1 can be reacted with dimethylcarbamoyl chloride to yield the dicarbamate of Compound 1. It will be recognized by those practicing the art that varying the conditions of this reaction will allow the synthesis of dicarbamates and monocarbamates, i.e. modification of the 3- and/or 4-hydroxyl moieties of Compound 1, which can be isolated by a variety of chromatographic or crystallographic techniques.

Example 11

Method for the Synthesis of Glucosides of Compound 1 diglucoside of
Compound 1

Compound 1 can be reacted with protected bromoglucose analogs, for example acetic acid 3,4,5-triacetoxy-6-bromotetrahydropyran-2-ylmethyl ester, followed by deprotection under basic conditions, to yield the glucoside conjugates of Compound 1. It will be recognized by those practicing the art that varying the conditions of this reaction will allow the synthesis of monoglucosides and diglucosides, i.e. modification of the 3- or 4-hydroxyl moieties of Compound 1, which can be isolated by a variety of chromatographic or crystallographic techniques.

Example 12

Conversion of Ester Prodrugs to Compound 1 by Mouse Plasma

Figure 1:
FIG. 1. Model for the conversion of Compound 2 to Compound 1. Compound 2 and several other prodrugs of this Invention are esters of Compound 1. These compounds are substrates for esterases present in the blood and/or tissues of mammals, thereby producing the active SK inhibitor.
Figure 2:
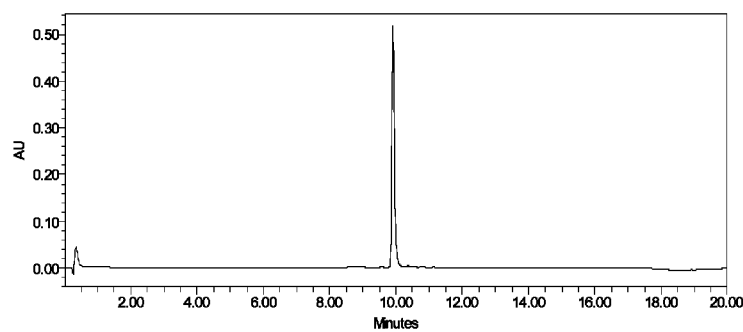
FIG. 2. Chromatogram of Compound 2. Purified Compound 2 was analyzed by high-performance liquid chromatography using a Waters 2795 system equipped with a photodiode array detector. Separations were conducted using a Nova-Pak C18 column (3.9×150 mm, Waters) eluted isocratically with a mobile phase that consisted of 65% Solvent A (methanol containing 0.1% formic acid) and 35% Solvent B (5% acetonitrile and 95% water containing 0.1% formic acid) at a flow rate of 0.6 mL/min. Compound 2 was detected by its absorbance at the wavelength of 265 nm. The data demonstrate that a single compound is initially present in the Compound 2 preparation.
Figure 3:
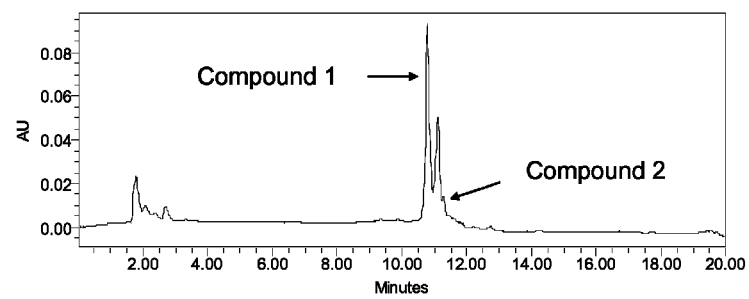
FIG. 3. Conversion of Compound 2 to Compound 1 by plasma enzymes. Purified Compound 2 was incubated with mouse plasma for 5 minutes at room temperature. The sample was then extracted and analyzed by high-performance liquid chromatography as described for FIG. 2. The data demonstrate that esterases in mouse plasma rapidly convert Compound 2 into Compound 1.

Prodrugs are compounds that are converted to a biologically active metabolite through the action of enzymes in the body. For example, as shown in FIG. 1, Compound 2 can be converted to Compound 1 by esterase activity in the blood and cells. In the case of alkyl esters, this conversion is commonly catalyzed by carboxyesterase 1. To demonstrate this conversion, Compound 2 was analyzed by High-Performance Liquid Chromatography (HPLC), and demonstrated to elute as a single well-defined peak (FIG. 2). When Compound 2 was incubated with plasma isolated from mouse blood at room temperature for 5 minutes and then analyzed by a similar HPLC process, the peak corresponding to Compound 2 was reduced by more than 95%, and new compounds that eluted with retention times consistent with the monoester of Compound 1, i.e. one of the acetyl esters had been removed, and Compound 1 itself, i.e. both of the acetyl esters had been removed (FIG. 3). Similar experiments with Compound 3, Compound 4, Compound 5 and Compound 6 demonstrated similar cleavage of the alkyl or amino acid esters resulting in the production of Compound 1. Therefore, consistent with the known metabolism of ester prodrugs, these compounds can effectively substitute for the active SK inhibitor, i.e. Compound 1, in biological experiments and therapeutic uses.

Example 13

Conversion of Compound 2 to Compound 1 in Living Mice

Figure 4:
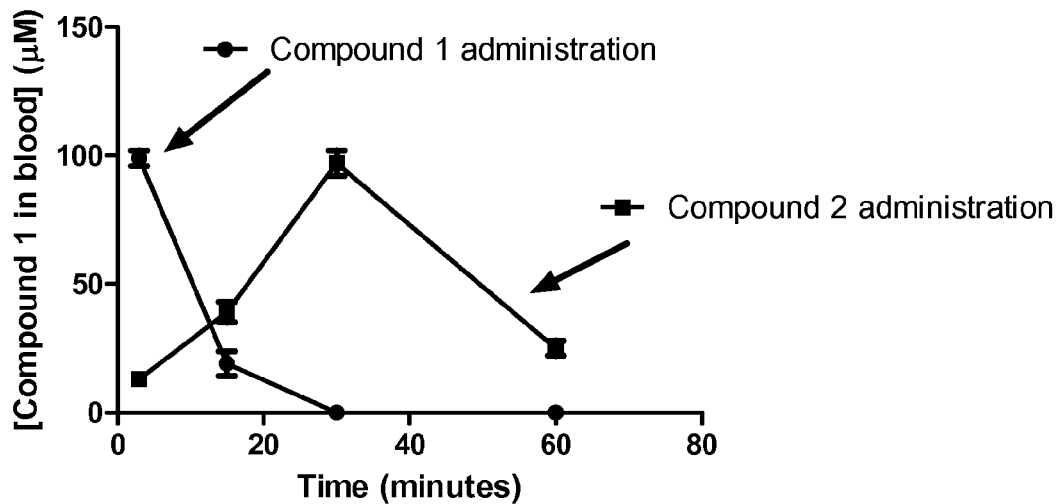
FIG. 4. Conversion of Compound 2 into Compound 1 in vivo. Balb/C female mice, 6-8 weeks old, were dosed with either Compound 1 (●) or Compound 2 (♦) at 50 mg/kg by intravenous injection. Mice were euthanized at the indicate times after injection, and blood was harvested by cardiac puncture and plasma was prepared. The plasma was then extracted and analyzed for Compound 1 levels by HPLC. The data demonstrate that the circulating levels of Compound 1 are maintained for a longer time by administration of the prodrug, i.e. Compound 2.

To extend the in vitro studies described above, the ability of Compound 2 to be converted to Compound 1 in an in vivo test system was determined. In these experiments, Compound 1 or Compound 2 was dissolved in PEG400 and administered to female Balb/C mice at a dose of 50 mg/kg by intravenous injection. Mice were sacrificed and blood was removed via cardiac puncture at 2 minutes, 15 minutes, 30 minutes or 60 minutes. The concentration of Compound 1 in the blood of the animals at each of the time points was determined using HPLC with UV detection as described in the previous Example. As shown in FIG. 4, these studies demonstrate that substantial amounts of Compound 1 can be detected in the blood after dosing. In the case of administration of Compound 1, the maximum plasma concentration was observed at the earliest time point, and Compound 1 concentrations were rapidly reduced, i.e. the half-time for clearance was approximately 5 minutes. In the case of administration of Compound 2, plasma concentrations of Compound 1 rose during the first 30 minutes and then were decreased with a half-time of clearance of approximately 20 minutes. This demonstrates that Compound 2 is efficiently converted to Compound 1 in the living animal, and the area-under-the-curve (AUC) for exposure to circulating Compound 1 is much greater when Compound 2 is used as the treating agent rather than Compound 1 itself. Therefore, it is expected that prodrugs of Compound 1 will be superior chemotherapeutic agents when long-term exposure is desired.

Example 14

Cytotoxicity Profiles of Compound 1 and Compound 2

Figure 5:
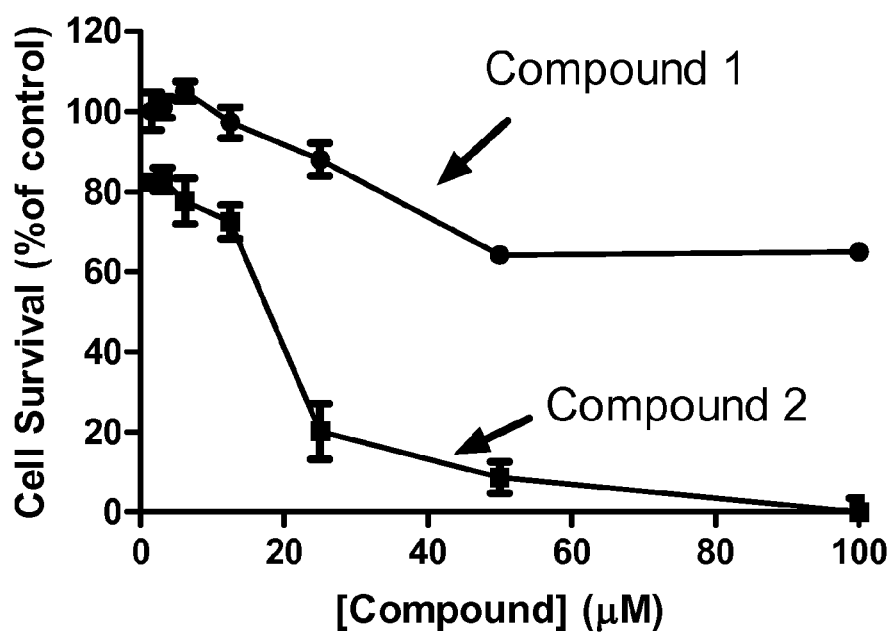
FIG. 5. Inhibition of tumor cell proliferation by Compound 1 and Compound 2. Murine JC mammary adenocarcinoma cells were exposed to the indicated concentrations of either Compound 1 (■) or Compound 2 (▲) for 72 hr. At the end of the exposure, the number of viable tumor cells was quantified using the MTS assay. Values represent the fraction of surviving cells compared with DMSO-(vehicle)-treated control cells. The data demonstrate that the prodrug form of Compound 1, i.e., Compound 2, has a higher potency (50% of cells are killed at a lower dose) and greater efficacy (a higher percentage of cells are killed at the optimal concentration) for inhibiting tumor cell proliferation.

To further assess the biological efficacies of the Compounds in intact cells, Compound 1 and Compound 2 were evaluated for cytotoxicity using a murine breast cancer cell line. These experiments followed methods that have been extensively used. The cells were treated with varying doses of the test Compound for 72 hours, and then cell viability was measured using CellTiter 96® AQueous Non-Radioactive Cell Proliferation Assay (MTS) available from Promega Corporation. The effects of the Compounds are shown in FIG. 5. Values represent the mean±std. dev. percentage of cells that survive at each of the indicated concentrations of Compound 1 or Compound 2. The data demonstrate that both Compounds can inhibit tumor cell proliferation. However, the extent of cell killing and the potency for cell killing were greater for Compound 2 than Compound 1. Therefore, the prodrug form is more effective at penetrating the cells and/or blocking proliferation.

Example 15

Antitumor Activity of Compound 2

Figure 6:
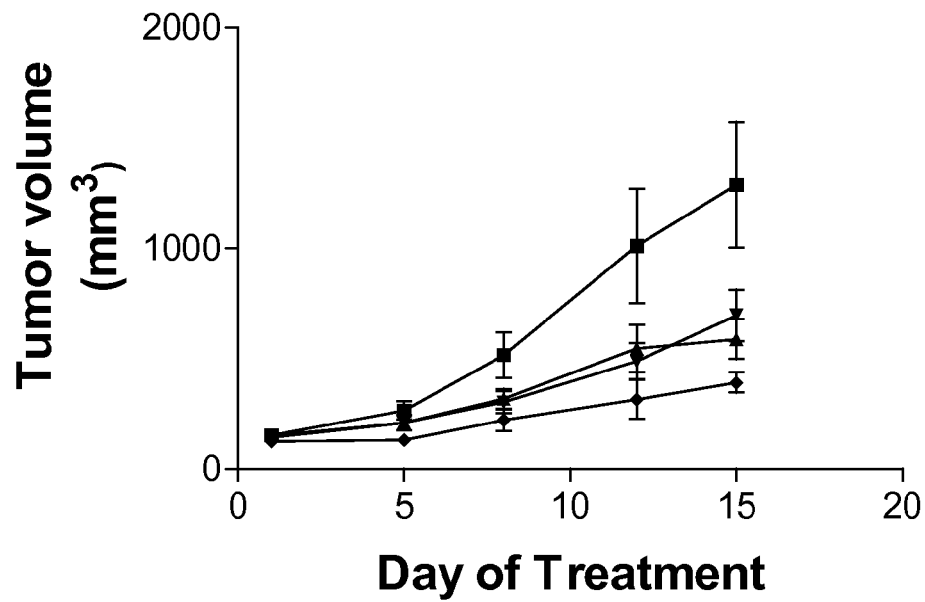
FIG. 6. Antitumor activity of Compound 2 alone and in combination with gemcitabine. Murine JC mammary adenocarcinoma cells were injected subcutaneously into Balb/c mice and tumors were allowed to grow to approximately 150 mm$^3$. The animals were then treated with vehicle alone (■), 1 mg/kg of gemcitabine weekly (▲), 50 mg/kg of Compound 2 daily for five days per week (▼) or a combination of gemcitabine plus Compound 2 (♦). Tumors were measured twice per week. The values shown represent the average tumor volume+/−the std. dev. for each group (n=8). The data demonstrate that Compound 2 alone causes significant reduction of tumor growth, and that the combination of Compound 2 plus gemcitabine has greater antitumor activity than either of the drugs alone.

The antitumor activity of a representative prodrug SK inhibitor was evaluated using a allogeneic tumor model that uses the mouse JC mammary adenocarcimona cell line growing subcutaneously in immunocompetent Balb/c mice (Lee et al., Oncol Res 14: 49 (2003)). These cells express elevated levels of SK activity relative to non-transformed cells, as well as the multidrug resistance phenotype due to P-glycoprotein activity. The data are shown in FIG. 6. Murine JC mammary adenocarcinoma cells were injected subcutaneously into Balb/c mice and tumors were allowed to grow to approximately 100 mm$^3$. The animals were then treated with vehicle alone (■), 1 mg/kg of gemcitabine weekly (▲), 50 mg/kg of Compound 2 daily for five days per week (▼) or a combination of gemcitabine plus Compound 2 (♦). Tumors were measured twice per week. The values shown represent the average tumor volume+/−the std. dev. for each group (n=8). The data demonstrate that Compound 2 alone causes significant reduction of tumor growth, and that the combination of Compound 2 plus gemcitabine has greater antitumor activity than either of the drugs alone.

Example 16

In Vivo Effects of Compound 1 and Compound 2 in a Model of Inflammatory Bowel Disease We have conducted experiments with Compound 1 and Compound 2 using the dextran sulfate sodium (DSS) model of IBD. In these experiments, male C57BL/6 mice were provided with standard rodent diet and water ad libitum. After their acclimation, the animals were randomly divided into groups of 5 or 6 for DSS (40,000 MW from ICN Biomedicals, Inc., Aurora, Ohio)- and drug-treatment. The Compounds were dissolved in a Vehicle consisting of 46.7% PEG 400, 46.7% of a solution of 0.375% Tween 80 in saline and 6.6% ethanol, and given once daily (starting on Day 0) by oral gavage in a volume of 0.1 mL per dose. The mice were given normal drinking water or 2% DSS (starting on Day 0) and treated orally with Compound 1 or Compound 2 at a dose of 50 mg/kg daily. The body weight of each animal was measured each day, and the Disease Activity Index (DAI) was scored for each animal on Day 6. On Day 6, the animals were sacrificed by cervical dislocation and the entire colon was removed and measured to the nearest 0.1 cm. The distal 3 cm of the colons were used for biochemical analyses of inflammation markers.

Figure 7:
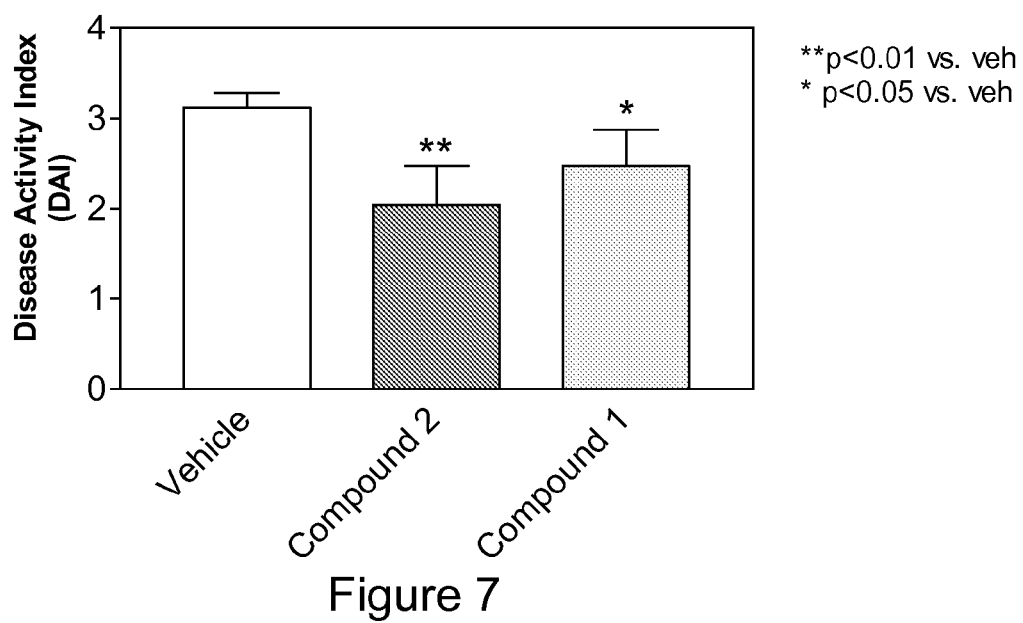
FIG. 7. Effects of Compound 1 and Compound 2 on the Disease Activity Index (DAI) in the acute DSS-colitis model. C57BL/6 mice were treated for 6 days as follows: 2% DSS in the drinking water and daily oral administration of Vehicle (46.7% PEG 400, 46.7% of a solution of 0.375% Tween 80 in saline and 6.6% ethanol); or 2% DSS in the drinking water and daily oral administration of 50 mg/kg Compound 1 or Compound 2 in Vehicle. After 6 days, the DAI was calculated for each group. Values represent the mean±std. dev. for 5-6 mice per group. The data demonstrate that both Compounds 1 and 2 reduce the severity of colitis in this model, with Compound 2 being more efficacious than Compound 1.

The DAI monitors weight loss, stool consistency and blood in the stool and is a measure of disease severity. Animals receiving normal drinking water and PEG as a solvent control had very low DAIs throughout the experiment. Exposure of the mice to DSS in their drinking water markedly induced IBD symptoms, including weight loss and the production of loose, bloody stools. The intensity of the disease progressively increased to the time the mice were sacrificed on Day 6. Treatment of the animals receiving DSS with either Compound 1 or Compound 2 reduced the intensity of the IBD manifestations in the mice (FIG. 7). Consistent with the data discussed above, Compound 2 was superior to Compound 1 in reducing the DAI for the mice.

Figure 8:
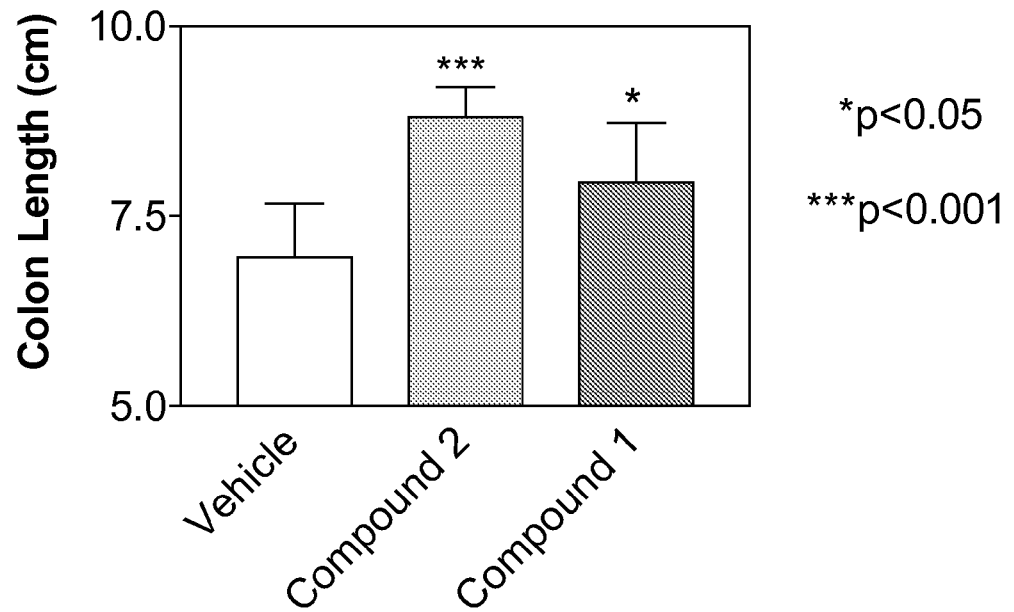
FIG. 8. Effects of Compound 1 and Compound 2 on colon length in the acute DSS-colitis model. C57BL/6 mice were treated for 6 days as follows: 2% DSS in the drinking water and daily oral administration of Vehicle (described in FIG. 7)

On Day 6, the animals were sacrificed by cervical dislocation and the entire colon was measured to assess shortening due to scarring and damage. Compared with the water control group, the colons of mice treated with DSS and vehicle were significantly shortened (FIG. 8). DSS-treated mice that were also treated with Compound 1 or Compound 2 had colons of significantly longer length, indicating substantial protection by the drugs. Again, the response to Compound 2 was superior to the protective effect of Compound 1.

Myeloperoxidase (MPO) activity, which is reflective of neutrophil influx into the colon, is often used as measure of inflammation, and was assayed in the colons of the mice from the DSS-colitis studies. As indicated in FIG. 9, MPO activity was highly elevated in the DSS-alone animals compared to water controls. The increase in MPO activity was markedly attenuated in mice receiving daily doses of either Compound 1 or Compound 2. As with the other markers of disease progression, the elevation of MPO activity was reduced to a greater extent in animals treated with Compound 2 compared with animals treated with Compound 1.

Example 17

In Vivo Effects of Ester Prodrugs in a Model of Inflammatory Bowel Disease

The DSS-model of ulcerative colitis was used to compare the anti-inflammatory activities of several additional ester prodrugs. As demonstrated in FIG. 10, Compounds 2, 3, 4, 5 and 6 were all effective in preventing the contraction of the colons of mice treated with DSS. Compound 4 was slightly less effective in this measure than the other ester prodrugs. To quantify the extent of colonic inflammation, MPO activity was measured in extracts from colons from the treated mice as described in the preceding Example. The data shown in FIG. 11 indicate that all of the Compounds except Compound 6 substantially prevented the elevation of colonic MPO activity resulting from the infiltration of granulocytes. Overall, these data demonstrate that the particular chemical entity which forms the protecting group (in this case, the ester) in the prodrug is not critical for the biological activity of the Compounds. Consequently, it is shown that a variety of prodrug forms of the active SK inhibitor can be used in the treatment of disease.

Example 18

In Vivo Effects of Compound 1 and Compound 2 in a Second Model of Inflammatory Bowel Disease The trinitrobenzene sulfonic acid (TNBS) model in rats provides a rapid, reliable and reproducible IBD model that mimics the manifestations of Crohn's Disease. Application of the hapten TNBS to the colon in the presence of ethanol results in transmural infiltrative disease that is limited to the colon and appears to be an IL-12-driven, Th1-mediated immunologic response. The role of TNFα in the development of the disease has been well-documented since the inflammatory response does not occur in TNFα-deficient animals and is markedly potentiated in mice that over-express this cytokine. TNBS induces measurable injury within 2 to 3 days, peak acute inflammation within a week, and gradual progression into chronic inflammation lasting about 2 months.

To test the efficacy of the Compounds, groups of female Sprague-Dawley rats were administered TNBS on Day 0 and treated with vehicle (as the negative control group), Compound 1 or Compound 2 on Days 0-5 by oral gavage at a dose of 50 mg/kg/day. There were no Compound-related toxicities apparent in rats sacrificed on Day 6 of these studies. Disease progression was evaluated by macroscopic score, colon weight and colon MPO activity at sacrifice. The macroscopic score measures macroscopic damage within the distal 6 cm of the colon using a system that considers the extent of and number of ulcerations. As shown in FIG. 12, Compound 2, but not Compound 1, reduced the Macroscopic Score in TNBS-treated rats. Similarly, Compound 2 but not Compound 1 reduced the elevation of the colon weight in TNBS-treated rats (FIG. 13) which results from edema, hypertrophy of the muscularis layer and fibrosis during inflammation. Finally, Compound 2 also reduced MPO activity in the colon (FIG. 14) confirming that it reduces granulocyte infiltration into the tissue. Together these data confirm the results seen in the DSS model, demonstrating that the prodrug form of the SK inhibitor has greater therapeutic efficacy than the active SK inhibitor itself.

What is claimed is:
1. A compound of the formula (I)

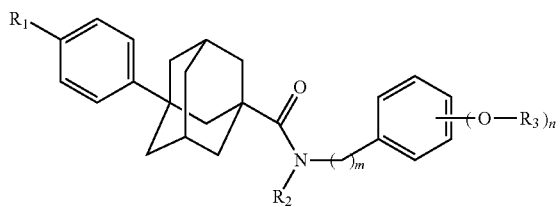

(I)

and pharmaceutically acceptable salts thereof, wherein
$R_1$ is H, Cl or F;
$R_2$ is H or alkyl;
m is 1 or 2;
n is 1, 2, 3, 4 or 5; and
each $R_3$ is independently H, —C(O)alkyl, —C(O)CH$_2$CH$_2$C(O)OH, $R_4$, —C(O)NR$_5$R$_6$, —P(O)(OR$_7$)$_2$ or glucosyl, provided that at least one $R_3$ is not H,
wherein
$R_4$ is a natural or unnatural amino acid linked through the carboxyl moiety as an ester,
$R_5$ is H or alkyl,
$R_6$ is H or alkyl, and
each $R_7$ is independently H or alkyl.
2. A compound according to claim 1, wherein $R_1$ is Cl.
3. A compound according to claim 1, wherein $R_2$ is H.
4. A compound according to claim 1, wherein m is 2.
5. A compound according to claim 1, wherein n is 1 or 2.
6. A compound according to claim 1, wherein n is 2.

7. A compound according to claim 1, wherein the

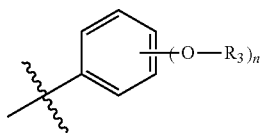

moiety has the structure

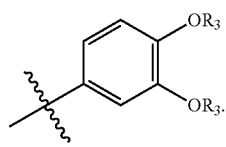

8. A compound according to claim 1, wherein each $R_3$ is a —C(O)alkyl.
9. A compound according to claim 7, wherein the

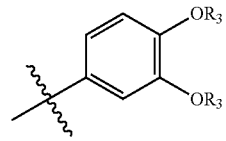

moiety has the structure

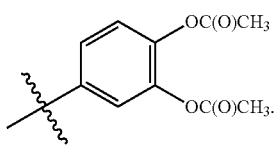

10. A compound according to claim 1, selected from the group consisting of:
acetic acid 2-acetoxy-5-(2-{[3-(4-chlorophenyl)-adamantane-1-carbonyl]-amino}ethyl)phenyl ester;
propionic acid 2-propionyloxy-5-(2-{[3-(4-chlorophenyl)-adamantane-1-carbonyl]-amino}ethyl)phenyl ester;
butyric acid 2-butyryloxy-5-(2-{[3-(4-chlorophenyl)-adamantane-1-carbonyl]-amino}ethyl)phenyl ester;
isobutyric acid 5-(2-{[3-(4-chlorophenyl)adamantane-1-carbonyl]amino}ethyl)-2-hydroxyphenyl ester; and
2-amino-3-methyl-butyric acid 5-(2-{[3-(4-chlorophenyl)adamantane-1-carbonyl]amino}ethyl)-2-hydroxyphenyl ester.
11. A compound according to claim 1, wherein the compound is acetic acid 2-acetoxy-5-(2-{[3-(4-chlorophenyl)-adamantane-1-carbonyl]-amino}ethyl)phenyl ester.
12. A pharmaceutical composition comprising a compound according to claim 1, or a pharmaceutically acceptable salt, hydrate or solvate thereof, in combination with a pharmaceutically acceptable carrier, medium, or auxiliary agent.
13. A method of inhibiting sphingosine kinase in a patient in need of such inhibition, the method comprising administering to the patient a compound or salt according to claim 1.
14. A method for treating a disease selected from a hyperproliferative disease, an inflammatory disease, or an angiogenic disease comprising administering to the patient a therapeutically effective amount of a compound or salt according to claim 1.

15. The method according to claim 14, wherein the disease is a hyperproliferative disease selected from the group consisting of cancer, atherosclerosis, restenosis, mesangial cell proliferative disorders, and psoriasis.

16. The method according to claim 15, wherein the hyperproliferative disease is a cancer selected from the group consisting of head and neck cancers, lung cancers, gastrointestinal tract cancers, breast cancers, gynecologic cancers, testicular cancers, urinary tract cancers, neurological cancers, endocrine cancers, skin cancers, sarcomas, mediastinal cancers, retroperitoneal cancers, cardiovascular cancers, mastocytosis, carcinosarcomas, cylindroma, dental cancers, esthesioneuroblastoma, urachal cancer, Merkel cell carcinoma, paragangliomas, Hodgkin lymphoma, non-Hodgkin lymphoma, chronic leukemias, acute leukemias, myeloproliferative cancers, plasma cell dyscrasias, and myelodysplastic syndromes.

17. The method according to claim 15, wherein the hyperproliferative disease is a mesangial cell proliferative disorder selected from the group consisting of glomerulonephritis, diabetic nephropathy, malignant nephrosclerosis, thrombotic microangiopathy syndromes, transplant rejection, and glomerulopathies.

18. The method according to claim 14, wherein the disease is an inflammatory disease selected from the group consisting of inflammatory bowel disease, arthritis, atherosclerosis, asthma, allergy, inflammatory kidney disease, circulatory shock, ischemia-reperfusion injury, post-surgical organ failure, multiple sclerosis, chronic obstructive pulmonary disease, skin inflammation, periodontal disease, psoriasis and T cell-mediated diseases of immunity.

19. The method according to claim 18, wherein the inflammatory disease is an inflammatory bowel disease selected from the group consisting of ulcerative colitis, Crohn's Disease and indeterminate colitis.

20. The method according to claim 18, wherein the inflammatory disease is a T cell-mediated diseases of immunity selected from the group consisting of allergic encephalomyelitis, allergic neuritis, transplant allograft rejection, graft versus host disease, myocarditis, thyroiditis, nephritis, systemic lupus erthematosus, and insulin-dependent diabetes mellitus.

21. The method according to claim 18, wherein the inflammatory disease is an arthritis selected from the group consisting of rheumatoid arthritis, osteoarthritis, Caplan's Syndrome, Felty's Syndrome, Sjogren's Syndrome, ankylosing spondylitis, Still's Disease, Chondrocalcinosis, gout, rheumatic fever, Reiter's Disease and Wissler's Syndrome.

22. The method according to claim 18, wherein the inflammatory disease is an inflammatory kidney disease selected from the group consisting of glomerulonephritis, glomerular injury, nephrotic syndrome, interstitial nephritis, lupus nephritis, Goodpasture's disease, Wegener's granulomatosis, renal vasculitis, IgA nephropathy and idiopathic glomerular disease.

23. The method according to claim 18, wherein the inflammatory disease is a skin inflammation selected from the group consisting of psoriasis, atopic dermatitis, contact sensitivity and acne.

24. The method according to claim 14, wherein the disease is an angiogenic disease selected from the group consisting of diabetic retinopathy, arthritis, cancer, psoriasis, Kaposi's sarcoma, hemangiomas, myocardial angiogenesis, atherscelortic plaque neovascularization, and ocular angiogenic diseases such as choroidal neovascularization, retinopathy of prematurity (retrolental fibroplasias), macular degeneration, corneal graft rejection, rubeosis, neuroscular glacoma and Oster Webber syndrome.

25. A compound according to claim 1, wherein $R_1$ is Cl, $R_2$ is H, and n is 1 or 2.

26. A compound according to claim 1, wherein each $R_3$ is independently H, —C(O)alkyl, —C(O)CH$_2$CH$_2$C(O)OH, $R_4$, —C(O)NR$_5$R$_6$, —P(O)(OR$_7$)$_2$ or glucosyl, provided that at least one $R_3$ is not H.

27. A compound of the formula (I)

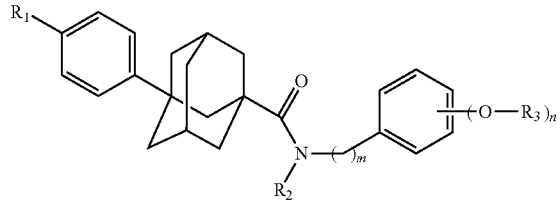

and pharmaceutically acceptable salts thereof, wherein
$R_1$ is H, Cl or F;
$R_2$ is H or alkyl;
m is 0, 1 or 2;
n is 2, 3, 4 or 5; and
each $R_3$ is independently H, —C(O)alkyl, —C(O)CH$_2$CH$_2$C(O)OH, $R_4$, —C(O)NR$_5$R$_6$, —P(O)(OR$_7$)$_2$ or glucosyl, provided that at least one $R_3$ is not H,
wherein
$R_4$ is a natural or unnatural amino acid linked through the carboxyl moiety as an ester,
$R_5$ is H or alkyl,
$R_6$ is H or alkyl, and
each $R_7$ is independently H or alkyl.

28. A compound of the formula (I)

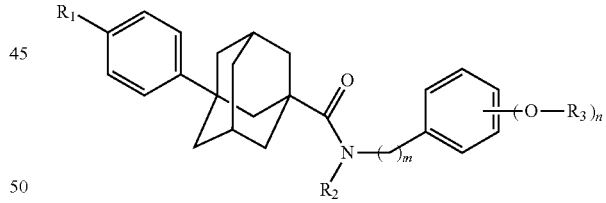

and pharmaceutically acceptable salts thereof, wherein
$R_1$ is H, Cl or F;
$R_2$ is H or alkyl;
m is 0, 1 or 2;
n is 1, 2, 3, 4 or 5; and
each $R_3$ is independently H, —C(O)CH$_2$CH$_2$C(O)OH, $R_4$, —C(O)NR$_5$R$_6$, —P(O)(OR$_7$)$_2$ or glucosyl, provided that at least one $R_3$ is not H,
wherein
$R_4$ is a natural or unnatural amino acid linked through the carboxyl moiety as an ester,
$R_5$ is H or alkyl,
$R_6$ is H or alkyl, and
each $R_7$ is independently H or alkyl.

* * * * *

UNITED STATES PATENT AND TRADEMARK OFFICE
CERTIFICATE OF CORRECTION

PATENT NO. : 8,685,936 B2  Page 1 of 1
APPLICATION NO. : 13/255813
DATED : April 1, 2014
INVENTOR(S) : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 205 days.

Signed and Sealed this

Twenty-ninth Day of September, 2015

Michelle K. Lee
*Director of the United States Patent and Trademark Office*